US008343539B2

(12) United States Patent
Kokkoli et al.

(10) Patent No.: US 8,343,539 B2
(45) Date of Patent: Jan. 1, 2013

(54) COMPOUNDS THAT BIND $\alpha_5\beta_1$ INTEGRIN AND METHODS OF USE

(75) Inventors: Efrosini Kokkoli, Minneapolis, MN (US); Anastasia Mardilovich, Minneapolis, MN (US); Ashish Garg, Falcon Heights, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 876 days.

(21) Appl. No.: 12/373,775

(22) PCT Filed: Jul. 13, 2007

(86) PCT No.: PCT/US2007/016046
§ 371 (c)(1),
(2), (4) Date: Jan. 14, 2009

(87) PCT Pub. No.: WO2008/008523
PCT Pub. Date: Jan. 17, 2008

(65) Prior Publication Data
US 2009/0280165 A1   Nov. 12, 2009

Related U.S. Application Data

(60) Provisional application No. 60/831,037, filed on Jul. 14, 2006.

(51) Int. Cl.
*A61K 9/127* (2006.01)
(52) U.S. Cl. ......... 424/450; 435/375; 514/1.1; 530/324; 530/326
(58) Field of Classification Search .................. None
See application file for complete search history.

(56) References Cited

U.S. PATENT DOCUMENTS

| | | | |
|---|---|---|---|
| 4,186,183 A | 1/1980 | Steck et al. |
| 4,217,344 A | 8/1980 | Vanlerberghe et al. |
| 4,485,054 A | 11/1984 | Mezei et al. |
| 4,774,085 A | 9/1988 | Fidler |
| 5,013,556 A | 5/1991 | Woodle et al. |
| 5,366,881 A | 11/1994 | Singh et al. |
| 5,891,468 A | 4/1999 | Martin et al. |
| 5,932,539 A | 8/1999 | Stupp et al. |
| 6,096,863 A | 8/2000 | Fields et al. |
| 6,475,808 B1 | 11/2002 | Wagner et al. |
| 6,500,453 B2 | 12/2002 | Brey et al. |
| 6,835,394 B1 | 12/2004 | Discher et al. |
| 7,101,570 B2 | 9/2006 | Hope et al. |
| 2005/0048110 A1 | 3/2005 | Discher et al. |
| 2005/0272662 A1 | 12/2005 | Stupp et al. |
| 2006/0240009 A1 | 10/2006 | Zalipsky et al. |
| 2007/0116753 A1 | 5/2007 | Hong et al. |

OTHER PUBLICATIONS

Kao, Biomaterials, 1999, vol. 20, pp. 2213-2221.*
American Type Culture Collection, "ATCC No. CCL-247," organism: *Homo sapiens* (human); designation: HCT 116; Manassas, VA; retrieved on Jan. 20, 2009 from the Internet; <URL:http://www.atcc.org/ATCCAdvancedCatalogSearch/ProductDetails/tabid/452/Default.aspx>; 3 pgs.
American Type Culture Collection, "ATCC No. CRL-2577," organism: *Homo sapiens* (human); designation: RKO; Manassas, VA; retrieved on Jan. 20, 2009 from the Internet; <URL:http://www.atcc.org/ATCCAdvancedCatalogSearch/ProductDetails/tabid/452/Default.aspx>; 2 pgs.
American Type Culture Collection, "ATCC No. CRL-2638," organism: *Mus musculus* (mouse); designation: CT26.WT; Manassas, VA; retrieved on Jan. 20, 2009 from the Internet; <URL:http://www.atcc.org/ATCCAdvancedCatalogSearch/ProductDetails/tabid/452/Default.aspx>; 2 pgs.
Agrawal et al., "Biodegradable polymeric scaffolds for musculoskeletal tissue engineering," *J. Biomed. Mater. Res.*, 2001;55(2):141-150.
Akiyama et al., "Function and receptor specificity of a minimal 20 kilodalton cell adhesive fragment of fibronectin," *Cell Adhes. Commun.*, 1995;3(1):13-25.
Allen et al., "Liposomes containing synthetic lipid derivatives of poly(ethylene glycol) show prolonged circulation half-lives in vivo," *Biochim. Biophys. Acta*, Jul. 1, 1991;1066(1):29-36.
Aota et al., "The short amino acid sequence Pro-His-Ser-Arg-Asn in human fibronectin enhances cell-adhesive function," *J. Biol. Chem.*, Oct. 7, 1994;269(40):24756-24761.
Aucoin et al., "Interactions of corneal epithelial cells and surfaces modified with cell adhesion peptide combinations," *J. Biomater. Sci. Polym. Ed.*, 2002;13(4):447-462.
Benoit et al., "The effect on osteoblast function of colocalized RGD and PHSRN epitopes on PEG surfaces," *Biomaterials*, Sep. 2005;26(25):5209-5220.
Berndt et al., "Synthetic lipidation of peptides and amino acids: monolayer structure and properties," *J. Am. Chem. Soc.*, Sep. 1995;117(37):9515-9522.
Castner et al., "Biomedical surface science: Foundations to frontiers," *Surf. Sci.*, Mar. 10, 2002;500(1-3):28-60 (available online on Feb. 21, 2002).
Chen et al., "Metastatic properties of prostate cancer cells are controlled by VEGF," *Cell Commun. Adhesion*, Jan.-Feb. 2004;11(1):1-11.
Chen et al., "Microdetermination of Phosphorus," *Analytical Chemistry*, Nov. 1956;28(11):1756-1758.
Childs, "The determination of polyethylene glycol in gamma globulin solutions," *Microchemical Journal*, Jun. 1975;20(2):190-192.
Cutler et al., "Engineering cell adhesive surfaces that direct integrin alpha5beta1 binding using a recombinant fragment of fibronectin," *Biomaterials*, May 2003;24(10):1759-1770.
Dankers et al., "A modular and supramolecular approach to bioactive scaffolds for tissue engineering," *Nature Mater.*, Jul. 2005;4(7):568-574 (published online on Jun. 19, 2005).
Davison et al., "Integrin alpha5beta1-mediated adenovirus infection is enhanced by the integrin-activating antibody TS2/16," *J. Virol.*, Aug. 1997; 71(8):6204-6207.

(Continued)

*Primary Examiner* — Christopher R Tate
*Assistant Examiner* — Roy Teller
(74) *Attorney, Agent, or Firm* — Mueting Raasch & Gebhardt, P.A.

(57) ABSTRACT

The present invention provides biologically active compounds that bind an $\alpha_5\beta_1$ integrin. Also included in the present invention are methods for using such biologically active compounds.

35 Claims, 12 Drawing Sheets

OTHER PUBLICATIONS

Dillow et al., "Adhesion of alpha5beta1 receptors to biomimetic substrates constructed from peptide amphiphiles," *Biomaterials*, Jun. 2001;22(12):1493-1505.

Ellis, "A targeted approach for antiangiogenic therapy of metastatic human colon cancer," *Am. Surg.*, Jan. 2003;69(1):3-10.

Fenske et al., "Encapsulation of weakly-basic drugs, antisense oligonucleotides,and plasmid DNA within large unilamellar vesicles for drug delivery applications," Chapter 6 in *Liposomes*, Eds. Torchilin et al., 2d ed., Oxford University Press, New York, NY, 2003, pp. 167-191.

Fields et al., "Solid phase peptide synthesis utilizing 9-fluorenylmethoxycarbonyl amino acids," *Int. J. Peptide Protein Res.*, Mar. 1990;35(3):161-214.

Fiske et al., "The Colorimetric Determination of Phosphorus," *Journal of Biological Chemistry*, Dec. 1925;66(2),375-400.

Freed et al., "Culture of organized cell communities," *Adv. Drug Deliver. Rev.*, Aug. 3, 1998;33(1-2):15-30.

Garcia et al., "Modulation of cell proliferation and differentiation through substrate-dependent changes in fibronectin conformation," *Mol. Biol. Cell*, Mar. 1999;10(3):785-798.

Garg et al., "Functionalized Liposomes for Targeting Colorectal Cancer," AIChE Annual Meeting in "Micro- and Nanodevices for Targeted Therapeutics I Session," San Francisco, California, Nov. 16, 2006; presentation and abstract; 21 pages.

Garg et al., "Integrin alpha(5)beta(1) Targeted Delivery to Colon Cancer Cells," Design of Medical Devices Conference, Minneapolis, Minnesota, Apr. 17-19, 2007; poster and abstract; 3 pages.

Gebicki et al., "Peroxidation of proteins and lipids in suspensions of liposomes, in blood serum, and in mouse myeloma cells," *Acta Biochimica Polonica*,2000;47(4):901-911.

Gong et al., "Role of alpha 5 beta 1 integrin in determining malignant properties of colon carcinoma cells," *Cell Growth Differ.*, Jan. 1997;8(1):83-90.

Grant et al., "Structural requirements for biological activity of the ninth and tenth FIII domains of human fibronectin," *J. Biol. Chem.*, Mar. 7, 1997;272(10):6159-6166.

Greenberg et al., "Prostate cancer in a transgenic mouse," *Proc. Natl. Acad. Sci. USA*, Apr. 1995;92:3439-3443.

Griffith, "Polymeric biomaterials," *Acta. Mater.*, Jan. 1, 2000, 48(1):263-277 (available online Jan. 24, 2000).

Hansma et al., "Analysis of matrix dynamics by atomic force microscopy,"*Methods Cell Biol.*, 2002;69:163-193.

Hartgerink et al., "Self-Assembly and Mineralization of Peptide-Amphiphile Nanofibers," *Science*, Nov. 23, 2001;294(5547):1684-1688.

Hartgerink et al., "Peptide-amphiphile nanofibers: A versatile scaffold for the preparation of self-assembling materials," *Proc. Natl. Acad. Sci. USA*, Apr. 16, 2002;99(8):5133-5138 (published online on Apr. 2, 2002).

Hubbell, "Biomaterials in tissue engineering," *Bio/Tech.*, Jun. 1995;13(6):565-576.

Hutmacher, "Scaffold design and fabrication technologies for engineering tissues—state of the art and future perspectives," *J. Biomat. Sci.-Polym. Ed.*,2001; 12(1):107-124.

Hynes, *Fibronectins*, Springer Verlag, New York, 1990; title page, copyright page, and table of contents only, 9 pgs.

Idiris et al., "Spring mechanics of alpha-helical polypeptide," *Protein Eng.*, Nov. 2000;13(11):763-770.

Ishida et al., "Liposome clearance," *Bioscience Reports*, Apr. 2002;22(2):197-224.

Jayne et al., "Extracellular matrix proteins and chemoradiotherapy: α5β1 integrin as a predictive marker in rectal cancer," *Euro. J. Surgical Oncology*, 2002;28(1):30-36 (available online Oct. 18, 2001).

Jensen et al., "Lipopeptides Incorporated into Supported Phospholipid Monolayers Have High Specific Activity at Low Incorporation Levels," *J. Am. Chem. Soc.*, 2004;126(46):15223-15230 (published on the web on Oct. 29, 2004).

Jia et al., "Integrin fibronectin receptors in matrix metalloproteinase-1-dependent invasion by breast cancer and mammary epithelial cells," *Cancer Res.*, Dec. 1, 2004;64(23):8674-8681.

Jockusch et al., "The molecular architecture of focal adhesions," *Annu. Rev. Cell Dev. Biol.*, Nov. 1995;11:379-416.

Kao, "Evaluation of protein-modulated macrophage behavior on biomaterials: designing biomimetic materials for cellular engineering," *Biomaterials*, 1999;20:2213-2221.

Kao et al., "Protein-mediated macrophage adhesion and activation on biomaterials: a model for modulating cell behavior," *J. Mater. Sci. Mater. Med.*, Oct.-Nov. 1999;10(10/11):601-605.

Kauf et al., "Recognition of fibronectin by the platelet integrin alpha IIb beta 3 involves an extended interface with multiple electrostatic interactions," *Biochemistry*, Aug. 7, 2001;40(31):9159-9166. Available online Jul. 13, 2001.

Kessner et al., "Investigation of the cellular uptake of E-Selectin-targeted immunoliposomes by activated human endothelial cells," *Biochim. Biophys. Acta*, Oct. 1, 2001;1514(2):177-190. Available online Sep. 6, 2001.

Kim et al., "Regulation of angiogenesis in vivo by ligation of integrin alpha5beta1 with the central cell-binding domain of fibronectin,"*Am. J. Path.*, Apr. 2000;156(4):1345-1362.

Kim et al., "Design and biological activity of synthetic oligopeptides with Pro-His-Ser-Arg-Asn (PHSRN) and Arg-Gly-Asp (RGD) motifs for human osteoblast-like cell (MG-63) adhesion," *Biotech. Let.*, Dec. 2002;24(24):2029-2033.

Kim et al., "Biomimetic approach on human periodontal ligament cells using synthetic oligopeptides," *J. Periodontal.*, Jul. 2004;75(7):925-932.

Kirpotin et al., "Liposomes with detachable polymer coating: destabilization and fusion of dioleoylphosphatidylethanolamine vesicles triggered by cleavage of surface-grafted poly(ethylene glycol)," *FEBS Lett.*, Jun. 17, 1996;388(2-3):115-118.

Klibanov et al., "Long-Circulating Liposomes: Development and Perspectives," *J. Liposome Research*, 1992;2(3):321-334. Available online Jan. 1, 1992.

Kokkoli et al., "Surface Pattern Recognition by a Colloidal Particle," *Langmuir*, Jan. 23, 2001;17(2):369-376 (published on web on Dec. 20, 2000).

Kokkoli et al., "Collective and single-molecule interactions of alpha5beta1 integrins," *Langmuir*, Mar. 16, 2004;20(6):2397-2404.

Kokkoli et al., "Fractalkine targeting with a receptor-mimicking peptide-amphiphile," *Biomacromolecules*, May-Jun. 2005;6(3):1272-1279.

Kokkoli et al., "Self-Assembly and Applications of Biomimetic and Bioactive Peptide-Amphiphiles", *Soft Matter*, 2006, 2(12): 1015-1024 (first published as an advance article on the web on Oct. 18, 2006).

Kokkoli et al., "Biomimetic Approaches to Biomaterials Design," AIChE Annual Meeting in "Bionanotechnology II: Plenary and Tutorial Session," Cincinnati, Ohio, Nov. 1, 2005; presentation and abstract; 34 pgs.

Kokkoli et al., "Designing Biomimetic Peptide-Amphiphiles for Targeted Cell Adhesion," Seminar at the Department of Chemical and Materials Engineering, University of Kentucky, Lexington, Kentucky, Nov. 16, 2005; presentation and abstract; 44 pgs.

Kokkoli et al., "Engineering Interfaces with Biomimetic Peptide-Amphiphiles for Controlled Cell Adhesion," MRS Fall Meeting in "Session: Engineered Biointerfaces I," Boston, Massachusetts, Nov. 30, 2005; presentation and abstract; 26 pgs.

Kokkoli et al., "AFM as a Tool for Engineering Biomimetic Peptide-Amphiphiles for Functional Interfaces," ACS Pacifichem in "Recent Developments in On-Site Instrumentation and Analysis Session," Honolulu, Hawaii, Dec. 15, 2005; presentation and abstract; 26 pgs.

Kokkoli et al., "Designing Biomimetic Peptides for Targeted Cell Adhesion," 3M Event, St. Paul, Minnesota, Mar. 17, 2006; presentation and abstract; 36 pgs.

Kokkoli et al., "Biomimetic Peptide-Amphiphiles for Targeted Drug Delivery," 3M Event, St. Paul, Minnesota, May 9, 2006; presentation and abstract; 27 pgs.

Kokkoli et al., "Biomimetic Peptide-Amphiphiles for Receptor-Targeted Therapeutics," IPRIME (Industrial Partnership for Research in Interfacial and Materials Engineering) Annual Meeting, University of Minnesota, Minneapolis, Minnesota, May 31, 2007; presentation and abstract; 18 pages.

Langer et al., "Designing materials for biology and medicine," *Nature*, Apr. 1, 2004;428(6982):487-492.

Leahy et al., "2.0 A crystal structure of a four-domain segment of human fibronectin encompassing the RGD loop and synergy region," *Cell*, Jan. 12, 1996;84(1):155-164.

Lee et al., "Quantitative analysis of liposome-cell interactions in vitro: rate constants of binding and endocytosis with suspension and adherent J774 cells and human monocytes," *Biochemistry*, Jan. 26, 1993;32(3):889-899.

Liu et al., "Role of cholesterol in the stability of pH-sensitive, large unilamellar liposomes prepared by the detergent-dialysis method," *Biochim. Biophys. Acta.*, Jun. 6, 1989;981(2):254-260.

Livant et al., "The PHSRN sequence induces extracellular matrix invasion and accelerates wound healing in obese diabetic mice," *J. Clin. Investig.*, Jun. 2000;105(11):1537-1545.

Mano et al., "Natural origin biodegradable systems in tissue engineering and regenerative medicine: present status and some moving trends," *J. R. Soc. Interface*, Dec. 22, 2007; 4(17):999-1030.

Mardilovich et al., "Biomimetic peptide-amphiphiles for functional biomaterials: the role of GRGDSP and PHSRN," *Biomacromolecules*, May-Jun. 2004;5(3):950-957.

Mardilovich, "Patterned biomimetic membranes: effect of concentration and pH," *Langmuir*, Aug. 2, 2005;21(16):7468-7475.

Mardilovich et al., "Design of a novel fibronectin-mimetic peptide-amphiphile for functionalized biomaterials," *Langmuir*, Mar. 28, 2006;22(7):3259-3264 (published on web on Feb. 23, 2006).

Mardilovich et al., "Biomimetic Peptide Amphiphiles for Specific Cell-Biomaterial Interactions," Gordon Research Conference "Biomaterials: Biocompatibility/Tissue Engineering" meeting, Plymouth, New Hampshire, Aug. 1-2, 2005; poster; 1 pg.

Mardilovich et al., "Design of Novel Biomimetic Peptide-Amphiphiles for Functional Biomaterials," AIChE Annual Meeting in "Biomimetic Interfaces Session," Cincinnati, Ohio, Nov. 4, 2005; presentation and abstract; 14 pgs.

Mardilovich et al., "Design of a Novel Fibronectin-Mimetic Peptide-Amphiphile for Functional Biomaterials," AIChE Annual Meeting in "Biomimetics I Session," San Francisco, California, Nov. 15, 2006; presentation and abstract; 21 pages.

Matter et al., "The alpha5beta1 integrin mediates elimination of amyloid-beta peptide and protects against apoptosis," *J. Cell Biol.*, May 18, 1998;141(4):1019-1030.

McIvor, R. Scott, "Transposon Mediated Gene Therapy for Colorectal Cancer," Grant Abstract, Grant No. 1R01CA120383-01A1 [online]. National Cancer Institute, project dates Jun. 29, 2007 to Apr. 30, 2012 [retrieved on Mar. 19, 2009]. Retrieved from the Internet<URL:http://crisp.cit.nih.gov/crisp/CRISP_LIB. getdoc?textkey=7197886&p_grant_num=1R01CA120383-01A1 &p_query=&ticket=90162987&p_audit_session_id=410693632 &p_keywords=>; 2 pgs.

Nag et al., "A colorimetric assay for estimation of polyethylene glycol and polyethylene glycolated protein using ammonium ferrothiocyanate," *Analytical Biochemistry*, Jun. 1, 1996;237(2):224-231.

Nag et al., "A colorimetric estimation of polyethyleneglycol-conjugated phospholipid in stealth liposomes," *Analytical Biochemistry*, Jul. 15, 1997;250(1):35-43.

Naughton, "From lab bench to market: critical issues in tissue engineering," *Ann. N. Y. Acad. Sci.*, Jun. 2002;961:372-385. Available online May 30, 2002.

Ochsenhirt et al., "Effect of RGD secondary structure and the synergy site PHSRN on cell adhesion, spreading and specific integrin engagement," *Biomaterials*, Jul. 2006;27(20):3863-3874 (published on web on Mar. 24, 2006).

Orsello et al., "Molecular properties in cell adhesion: a physical and engineering perspective" *Trends Biotechnol.*, Aug. 2001;19(8):310-316.

Papahadjopoulos et al., "Sterically stabilized liposomes: improvements in pharmacokinetics and antitumor therapeutic efficacy," *Proc. Natl. Acad. Sci. USA*, Dec. 15, 1991, 88(24): 11460-11464.

Papahadjopoulos et al., "Steric Stabilization: An Overview," Chapter 1 in *Liposomes: Rational Design*, Janoff, A. S. (Ed.), Marcel Dekker, New York, 1999, pp. 1-12.

Petrie, "Integrin specificity and enhanced cellular activities associated with surfaces presenting a recombinant fibronectin fragment compared to RGD supports," *Biomaterials*, Nov. 2006;27(31):5459-5470. Published online Jul. 18, 2006.

Pierschbacher et al., "Synthetic peptide with cell attachment activity of fibronectin," *Proc. Nat. Acad. Sci. USA*, Mar. 1983;80:1224-1227.

Redick et al., "Defining fibronectin's cell adhesion synergy site by site-directed mutagenesis," *J. Cell Biol.*, Apr. 17, 2000;149(2):521-527.

Ruoslahti et al., "Anchorage dependence, integrins, and apoptosis," *Cell*, May 20, 1994; 77(4):477-478.

Sachlos et al., "Making tissue engineering scaffolds work. Review on the application of solid freeform fabrication technology to the production of tissue engineering scaffolds," *Europ. Cells Materials*, 2003;5:29-40.

Selisko et al., "Analysis and purification of monomethoxy-polyethylene glycol by vesicle and gel peiineation chromatography," *Journal of Chromatography A*, Jul. 2, 1993;641(1):71-79.

Semler et al., "Cytomimetic engineering of hepatocyte morphogenesis and function by substrate-based presentation of acellular E-cadherin," *Tissue Engineering*, May-Jun. 2005;11(5-6):734-750.

Shimada et al., "Determination of incorporated amounts of poly(ethylene glycol)-derivatized lipids in liposomes for the physicochemical characterization of stealth liposomes," *International Journal of Pharmaceutics*, Aug. 10, 2000;203(1-2):255-263.

Simoes et al., "On the formulation of pH-sensitive liposomes with long circulation times," *Advanced Drug Delivery Reviews*, Apr. 23, 2004;56(7):947-965.

Sims et al., "A method for the estimation of polyethylene glycol in plasma protein fractions," *Analytical Biochemistry*, Sep. 1, 1980;107(1):60-63.

Skoog, "Determination of polyethylene glycols 4000 and 6000 in plasma protein preparations," *Vox Sanguinis*, 1979;37(6):345-349.

Slepushkin et al., "Sterically stabilized pH-sensitive liposomes. Intracellular delivery of aqueous contents and prolonged circulation in vivo," *J. Biol. Chem.*, Jan. 24, 1997;272(4):2382-2388.

Susuki et al., "Preparation and biological activities of a bivalent poly(ethylene glycol) hybrid containing an active site and its synergistic site of fibronectin," *Chem. Pharm. Bull.* (Tokyo), Sep. 2002;50(9):1229-1232.

Terramani et al., "Human macrovascular endothelial cells: optimization of culture conditions," *In Vitro Cell Dev. Biol.—Animal*, Feb. 2000;36(2):125-132.

Tirrell et al., "The role of surface science in bioengineered materials," *Surf. Sci.*, Mar. 10, 2002;500(1-3):61-83 (available online Feb. 21, 2002).

Tsukamoto et al., "Expression of the int-1 gene in transgenic mice is associated with mammary gland hyperplasia and adenocarcinomas in male and female mice," *Cell*, Nov. 18, 1988;55(4):619-625.

van Golen et al., "Suppression of tumor recurrence and metastasis by a combination of the PHSCN sequence and the antiangiogenic compound tetrathiomolybdate in prostate carcinoma," *Neoplasia*, Sep.-Oct. 2002;4(5):373-379.

Varner et al., "Integrins and cancer," *Curr. Opin. Cell Biol.*, Oct. 1996;8(5):724-730.

Wang et al., "pH-sensitive immunoliposomes mediate target-cell-specific delivery and controlled expression of a foreign gene in mouse," *Proc. Natl. Acad. Sci. USA.*, Nov. 1987;84(22):7851-7855.

Williams et al., "Conformational states of fibronectin. Effects of pH, ionic strength, and collagen binding," *J. Biol. Chem.*, Dec. 25, 1982;257(24):14973-14978.

Woodle et al., *Long Circulating Liposomes: Old Drugs, New Therapies*, ed. Strom, Springer, Berlin, Germany, 1998, title page, copyright page, and table of contents only, 8 pgs.

Wu et al., "The alpha 5 beta 1 integrin fibronectin receptor, but not the alpha 5 cytoplasmic domain, functions in an early and essential step in fibronectin matrix assembly," *J. Biol. Chem.*, Oct. 15, 1993;268(29):21883-21888.

Yang et al., "Human osteoprogenitor growth and differentiation on synthetic biodegradable structures after surface modification," *Bone*, Dec. 2001;29(6):523-531.

Zhang et al., "The alpha v beta 1 integrin functions as a fibronectin receptor but does not support fibronectin matrix assembly and cell migration on fibronectin," *J. Cell Biol.*, Jul. 1993;122(1):235-242.

\* cited by examiner

COMPOUNDS THAT BIND α₅β₁ INTEGRIN AND METHODS OF USE

CONTINUING APPLICATION DATA

This application is a U.S. National Stage Application of International Application No. PCT/US2007/016046, filed 13 Jul. 2007, published in the English language on Jan. 17, 2008 as International Publication No. WO 2008/008523 A1, which claims the benefit of U.S. Provisional Application No. 60/831,037, filed 14 Jul. 2006, both of which are hereby incorporated by reference in their entirety.

BACKGROUND

Materials employed in biomedical technology are increasingly being designed to have specific, desirable biological interactions with their surroundings, as opposed to the older, more common practice of trying to adapt traditional materials to biomedical applications. A common theme in engineering cell and tissue behavior at device surfaces is to modify the material's interface to interact selectively with a specific cell type through biomolecular recognition events. The cell surface has a variety of receptors that bind with other cells or specific proteins, which compose the environment (known as the extracellular matrix, ECM) surrounding the cells. A promising approach is the biomimetic modification of the material, in which peptides, or recombinant protein fragments containing the adhesion domains of the ECM proteins, are attached to the interface (Hubbell, *Bio-tech.*, 1995; 13:565-576; Castner et al., *Surf Sci.*, 2002; 500:28-60; Hartgerink et al., *Proc. Nat. Acad. Sci. USA*, 2002; 99:5133-5138; Tirrell et al., *Surf Sci.*, 2002; 500:61-83; Cutler et al., *Biomaterials*, 2003; 24:1759-1770; Jensen et al., *J. Am. Chem. Soc.*, 2004; 126:15223-15230; Langer et al., *Nature*, 2004; 428: 487-492; Dankers et al., *Nature Mater.*, 2005; 4:568-574; Semler et al., *Tissue Engineering*, 2005; 11:734-750; Orsello et al., *Trends Biotechnol.*, 2001; 19:310-316).

The precise control of cell adhesion and migration in the body aids biological processes such as embryogenesis, homeostasis, the immune response, and tissue remodeling and healing (Hynes, *Fibronectins*, Springer Verlag, New York, 1990; Ruoslahti et al., *Cell*, 1994; 77). Central to this control is the integrin-mediated adhesion to proteins from the ECM. Although integrins and in particular the α₅β₁ integrin were originally characterized as a family of cell adhesion receptors that are responsible for anchoring cells to ECM, they have recently been shown to have a dramatic impact on dynamic processes such as mediating adenovirus infection, accelerating wound healing, providing a protection mechanism against Alzheimer's disease, and acting as a promising target for breast, colon, prostate, and rectal cancer (Vainer et al., *Curr. Opin. Cell Biol.*, 1996; 8:724-730; Davison et al., *J. Virol.*, 1997; 71:6204-6207; Matter et al., *J. Cell Biol.*, 1998; 141:1019-1030; Livant et al., *J. Clin. Investig.*, 2000; 105: 1537-1545; van Golen et al., *Neoplasia*, 2002; 4:373-379; Kim et al., *Am. J. Path.*, 2000; 156:1345-1362; Gong et al., *Cell Growth Differ.*, 1997; 8:83-90; Jayne et al., *EJSO*, 2002; 28:30-36; Ellis, Am. Surgeon, 2003; 69:3-10; Jia et al., *Cancer Res.*, 2004; 64:8674-8681; Chen et al., *Cell Commun. Adhesion*, 2004; 11:1-11).

Many therapeutic strategies require the use of peptides, such as the short sequence arginine-glycine-aspartic acid (RGD), that mimic the cell adhesion domain of fibronectin in an attempt to target the α₅β₁ integrin and provide treatment. Even though surface modification with a biomimetic peptide remains one of the most promising strategies, the therapeutic use of RGD-containing peptides has been limited since they cannot accurately mimic the affinity of fibronectin for the α₅β₁ integrin (Pierschbacher et al., *Proc. Nat. Acad. Sci. USA*, 1983; 80:1224-1227; Yang et al., *Bone*, 2001; 29:523-531; Akiyama et al., *Cell Adhes. Commun.*, 1995; 3:13-25). This may be due to the fact that RGD peptides lack synergistic effects that come from the proline-histidine-serine-arginine-asparagine (PHSRN) site. Thus, the ability to design peptides that accurately mimic the fibronectin α₅β₁-mediated adhesion has increased therapeutic potential and represents a significant undertaking.

When RGD and PHSRN have been presented in a single peptide formulation in the past, results varied depending on the design. Motifs included no linker (Aucoin et al., *J. Biomater. Sci. Polym. Edn.*, 2002; 13:447-462), or linkers of varying number of glycine (G) amino acids ($G_3$-$G_{13}$) (Kao, *Biomaterials*, 1999; 20:2213-2221; Kim et al., *Biotech. Let.*, 2002; 24:2029-2033; Benoit et al., *Biomaterials*, 2005; 26:5209-5220), or a bivalent polyethylene glycol hybrid linker (Suzuki et al., *Chem. Pharm. Bull.*, 2002; 50:1229-1232). However, for short periods of time before cells start secreting their own ECM, the sequences that were compared to fibronectin showed adhesion strengths that are smaller than fibronectin. Moreover, one study that examined ECM production demonstrated that ECM secretion was the lowest on surfaces functionalized with the colocalized (RGDG$_{13}$PHSRN; SEQ ID NO: 11) peptide sequence compared to surfaces with a scrambled peptide sequence (RDGG$_{13}$HPRNS; SEQ ID NO: 12) or RGD, emphasizing the need to design peptides that are optimized to promote cell adhesion and encourage ECM production (Benoit et al., *Biomaterials*, 2005; 26:5209-5220).

SUMMARY OF THE INVENTION

The present invention provides biologically active compounds that include a headgroup X1X2X3RX4-linker-RGD. Preferably, a biologically active compound specifically binds an α₅β₁ integrin. X1, X2, X3, and X4 can be any amino acid. For instance, the X1 may be a serine, a proline, or a conservative substitution for proline, X2 may be a histidine, a proline, a glycine or a conservative substitution for histidine, X3 may be a serine, a glycine, or a conservative substitution for serine, and the X4 may be an asparagine, a glutamine, or a conservative substitution for asparagine. A preferred example of the X1X2X3RX4 is PHSRN.

The linker can include an amino acid sequence having any combination of amino acids, and is at least 29 Å in length. The amino acids of the linker may be hydrophobic or hydrophilic. For instance, the amino acids of the linker may be in a hydrophobic:hydrophilic ratio of between at least 0.5:1 and 1:at least 0.5. An example of a linker includes SGSGSGSGSG. An example of a headgroup includes PHSRNSGSGSGSGS-GRGDSP, and KSSPHSRNSGSGSGSGSGRGDSP.

A biologically active compound may further include a spacer, such as KSS, attached to the amino terminus of the headgroup.

A biologically active compound may further include a tail attached to the headgroup. The tail may be, for instance, hydrophilic, hydrophobic, or amphipathic. A biologically active compound may further include spacer present between the tail and the headgroup. Also included in the present invention are compositions that include a biologically active compound. Such compositions may further include a pharmaceutically acceptable carrier.

Also provided herein are surfaces that include a biologically active compound of the present invention. The surface may be 2-dimensional or 3-dimensional. The biologically active compound may be covalently attached to the surface. The biologically active compound may be present on the surface at a concentration of between at least 0.5 mol % and no greater than 2.6 mol %.

The present invention further provides a vesicle having the biologically active compound of the present invention present on the surface of the vesicle. The biologically active compound may be present on the surface at a concentration of at least 0.5 mol % to no greater than 2.6 mol %. The surface of a vesicle may also include polyethylene glycol at a concentration of, for instance, between at least 0.5 mol % and no greater than 8 mol %. The vesicle may include a trigger that promotes destabilization of the vesicle, such as a pH sensitive trigger. The vesicle may include dioleoylphosphatidylethanolmaine. The vesicle may include a compartment having an aqueous liquid which may include an agent. The agent may be therapeutic or non-therapeutic. The vesicle may be present as a composition with, for instance, a pharmaceutically acceptable carrier.

Also included herein are methods for using a biologically active compound of the present invention. The methods include, for instance, contacting a membrane with a vesicle of the present invention, wherein the membrane includes an $\alpha_5\beta_1$ integrin. The membrane may be part of a cell, and the cell may be ex vivo or in vivo.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a process chamber that comprises "an" amplification enzyme can be interpreted to mean that the process chamber includes "one or more" amplification enzymes.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list. Furthermore, various embodiments are described in which the various elements of each embodiment could be used in other embodiments, even though not specifically described.

DETAILED DESCRIPTION OF ILLUSTRATIVE EMBODIMENTS

Figure 1:
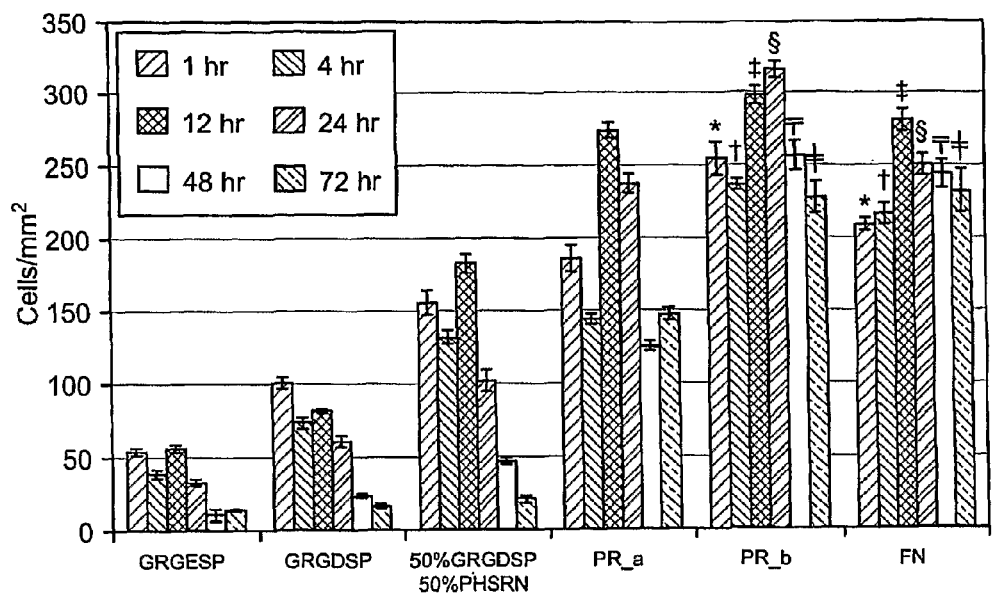
FIG. 1. Effect of time and surface composition on HUVEC adhesion. Cell adhesion was evaluated on LB membranes of the following peptide-amphiphiles: GRGDSP, 50% GRGDSP-50% PHSRN, PR_a, and PR_b. The GRGESP (SEQ ID NO:6) peptide-amphiphile was used as a negative control and FN substrates as a positive control. HUVECs were incubated on these substrates for 1-72 hours at 37° C., 5% $CO_2$, in the absence of fetal bovine serum. The initial cell density was 497 cells/mm$^2$. The PR_b peptide-amphiphile outperforms all other peptide surfaces and compared to the positive control, FN, gives higher adhesion for 1-24 hours (z-test analysis for *, †, ‡, §, p<0.007) and similar adhesion for 48-72 hours (z-test analysis for ⊤,⊥, , p<0.1, signifying no statistical difference). Each histogram represents the mean±SD. For all substrates n=2 (two independent experiments performed at different days).
Figure 2A:
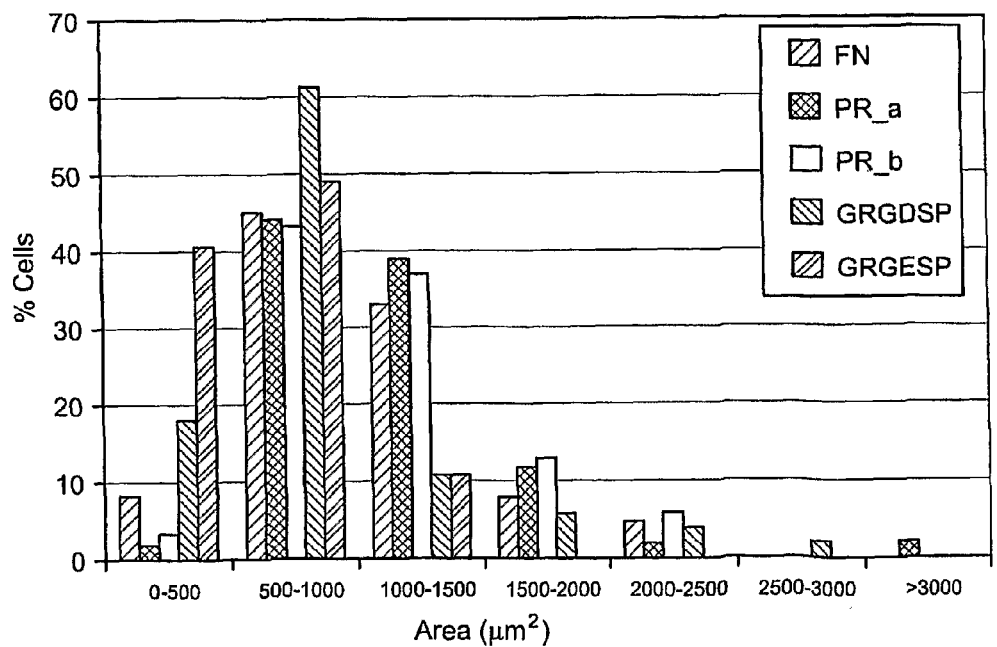
FIG. 2. Effect of time and surface composition on HUVEC spreading Cell spreading was evaluated on LB membranes of the following peptide-amphiphiles: GRGDSP, PR_a, and PR_b. The GRGESP (SEQ ID NO:6) peptide-amphiphile was used as a negative control and FN substrates as a positive control. HUVECs were incubated, in the absence of fetal bovine serum, at 37° C. and 5% $CO_2$, on these substrates for: a) 1 hr, b) 12 hours, c) 24 hours, and d) 72 hours. At 72 hours, only PR_a, PR_b, and FN substrates were evaluated as GRGDSP (SEQ ID NO:7) and GRGESP (SEQ ID NO:6) failed to sustain cell adhesion after 48 hours. Results are reported as percentage of cells spread within a cell area.
Figure 2B:
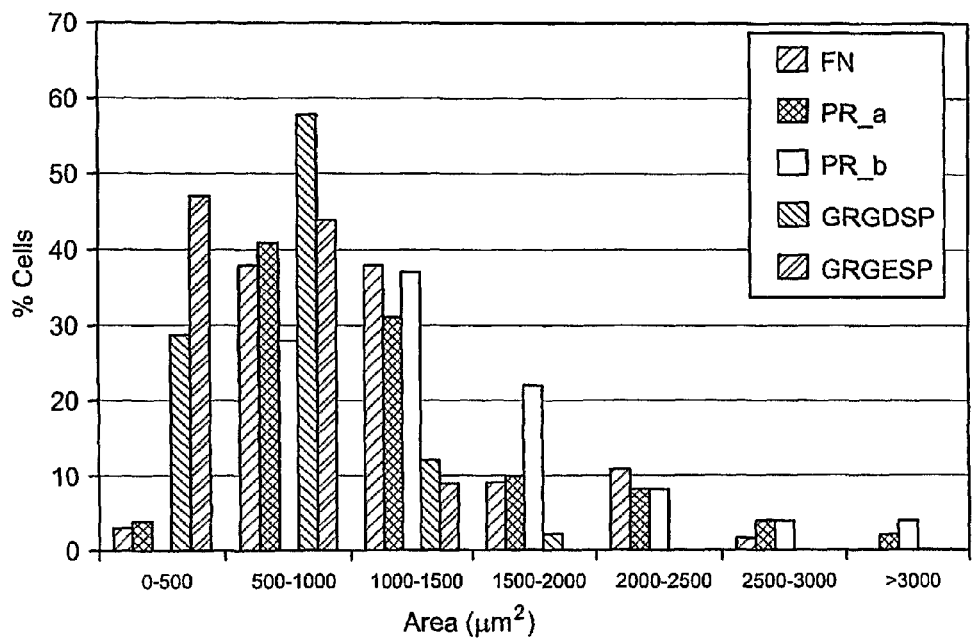
Figure 2C:
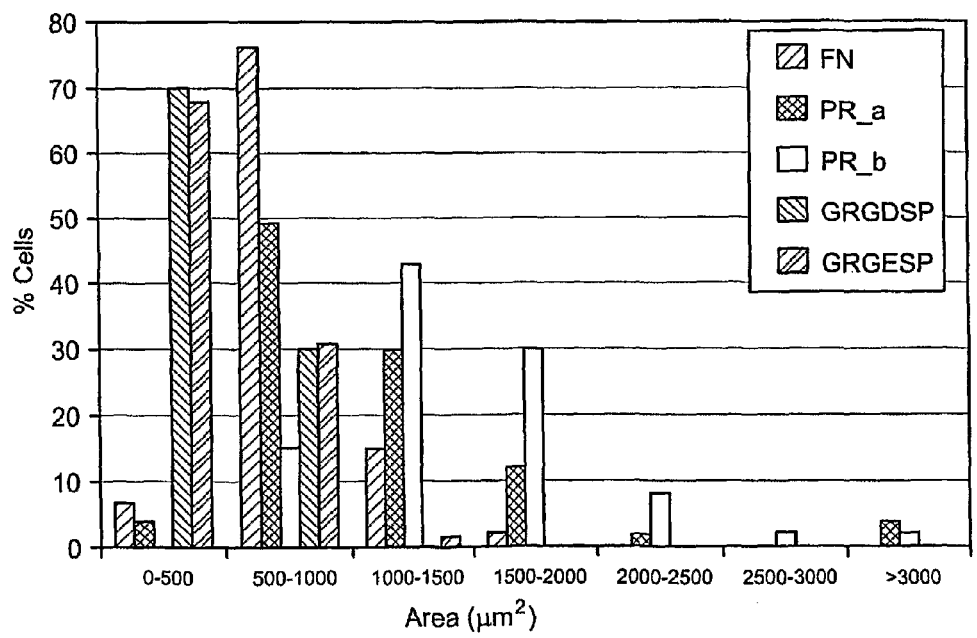
Figure 2D:
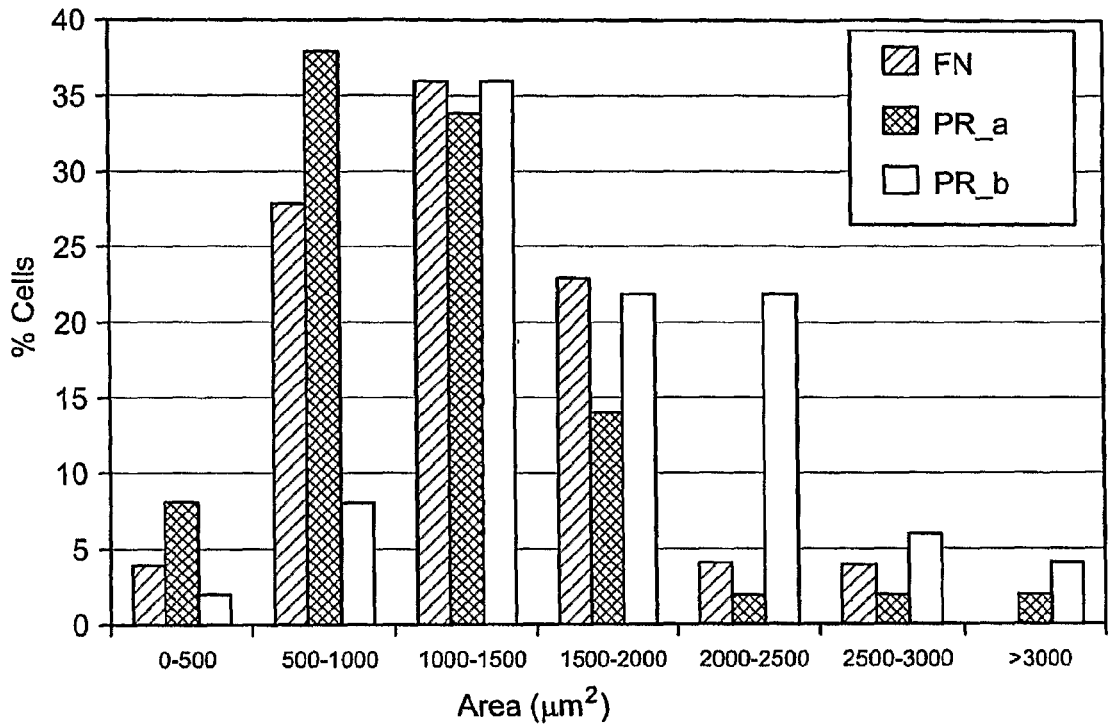

The present invention provides compounds that bind $\alpha_5\beta_1$ integrins. Integrins are a heterodimeric family of cell surface receptors that bind extracellular matrix ligands or other cell adhesion ligands and thereby mediate cell-cell and cell-matrix adhesion processes. Integrins include noncovalently associated α and β subunits. Fourteen α subunits and 8β subunits have been identified. Pairing of α and β subunits results in approximately 21 members of the integrin family of adhesion receptors. The $\alpha_5\beta_1$ integrin is the prototype fibronectin receptor, since it was the first one to be identified that bound fibronectin, and is specialized for binding the ligand fibronectin.

A compound of the present invention includes a headgroup having the following components: synergy site-linker-RGD. The synergy site, which is based on the normal synergy site PHSRN (SEQ ID NO: 10) present in human fibronectin, is X1 X2X3RX4 (SEQ ID NO: 1). The amino acids present at the X1, X2, X3, or X4 of a synergy site may be any combination of amino acids, provided the headgroup exhibits integrin $\alpha_5\beta_1$ binding activity. Methods for measuring such a binding activity are described herein.

For instance, in one aspect, the amino acid present at X1, X2, X3, or X4 may be a conservative substitution for the amino acid present in the normal synergy site. A conservative substitution is typically the substitution of one amino acid for another that is a member of the same class. For example, it is well known in the art of protein biochemistry that an amino acid belonging to a grouping of amino acids having a particular size or characteristic (such as charge, hydrophobicity, and/or hydrophilicity) can generally be substituted for another amino acid without substantially altering the secondary and/or tertiary structure of a polypeptide. For the purposes of this invention, conservative amino acid substitutions are defined to result from exchange of amino acids residues from within one of the following classes of residues: Class I: Gly, Ala, Val, Leu, and Ile (representing aliphatic side chains); Class II: Gly, Ala, Val, Leu, Ile, Ser, and Thr (representing aliphatic and aliphatic hydroxyl side chains); Class III: Tyr, Ser, and Thr (representing hydroxyl side chains); Class IV: Cys and Met (representing sulfur-containing side chains); Class V: Glu, Asp, Asn and Gln (carboxyl or amide group containing side chains); Class VI: His, Arg and Lys (representing basic side chains); Class VII: Gly, Ala, Pro, Trp, Tyr, Ile, Val, Leu, Phe and Met (representing hydrophobic side chains); Class VIII: Phe, Trp, and Tyr (representing aromatic side chains); and Class IX: Asn and Gln (representing amide side chains). The classes are not limited to naturally occurring amino acids, but also include artificial amino acids, such as beta or gamma amino acids and those containing non-natural side chains, and/or other similar monomers such as hydroxy-acids.

Thus, in some aspects of the present invention, the amino acid present at X1 may be a serine, a proline, or a conservative substitution for proline, preferably proline or serine, more preferably proline; the amino acid present at X2 may be a histidine, a proline, a glycine or a conservative substitution for histidine, more preferably a histidine, a proline, or a glycine, most preferably a histidine; the amino acid present at X3 may be a serine, a glycine, or a conservative substitution for serine, preferably serine or glycine, more preferably serine; the amino acid present at X4 may be an asparagine, a glutamine, or a conservative substitution for asparagine, preferably asparagine or glutamine, more preferably asparagine.

The linker of the headgroup is situated between the synergy site and the RGD. The linker serves to position the synergy site and the RGD at an appropriate distance from each other to allow the two regions to promote binding to $\alpha_5\beta_1$ integrins. This distance may be, but is not limited to, at least 29 angstroms (Å), preferably, at least 33 Å, more preferably, at least 35 Å, and no greater than 40 Å, preferably, no greater than 38 Å. The distance a linker will separate the synergy site and the RGD can be determined using routine methods. For instance, when the linker is made up of amino acids, the distance can be calculated by assuming each amino acid is 3.7 Å long (Idiris et al., *Protein Eng.*, 2000; 13:763-770, and Kokkoli et al., *Langmuir*, 2004; 20:2397-2404). A linker can include, but is not limited to, hydrophilic molecules (such as hydrophilic amino acids), hydrophilic molecules (such as hydrophobic amino acids), or a combination thereof. When a linker has hydrophilic and hydrophobic molecules, such as hydrophilic and hydrophobic amino acids, preferably the ratio of hydrophilic and hydrophobic amino acids is close to 1:1, which is similar to the ratio of hydrophilic and hydrophobic residues between the synergy site and the RGD in a fibronectin protein (Mardilovich et al., *Biomacromolecules*, 2004; 5:950-957). Examples of useful ratios include at least 0.5:1, 1:1, and 1:at least 0.5. Exemplary linkers include SGSGSGSG ((SG)$_4$; SEQ ID NO:2), SGSGSGSGSG ((SG)$_5$; SEQ ID NO:3), GGGGGGGGGG (SEQ ID NO:4), and SSSSSSSSSS (SEQ ID NO:5). Examples of other linkers include a varying number of glycine amino acids (for instance, between 3 glycines and 13 glycines). In general, when a linker includes amino acids, smaller amino acids are preferred over larger amino acids in some aspects of the present invention. An example of a linker that does not include amino acids is a bivalent poly (ethylene glycol) hybrid linker (Susuki et al., *Chem. Pharm. Bull.*, 2002; 50:1229-1232). In some aspects of the invention, the headgroup is hydrophilic, such as when the headgroup is part of an amphiphile. A preferred example of a headgroup is PHSRNSGSGSGSGSGRGDSP (SEQ ID NO:8).

The RGD region of the headgroup can optionally include additional components attached to the aspartic acid residue, provided the headgroup is still able to bind $\alpha_5\beta_1$ integrins. Examples of additional components include, but are not limited to, amino acids, such as amino acids with aliphatic side chains, aliphatic hydroxyl side chains, hydrophobic side chains, or a combination thereof. In one aspect, the amino acids serine-proline can be bound to the RGD to result in RGDSP.

Optionally, and preferably, a headgroup of the present invention also includes a structure, referred to as a spacer, connected to the synergy site. Spacers are discussed in greater detail below.

Optionally, and preferably, a compound of the present invention also includes a component attached to the amino terminal end of the headgroup. Such a component is referred to herein as a tail. The tail can permit a compound of the present invention to interact with other molecules. For instance, the tail can anchor a compound of the present invention to a surface, or can permit a compound of the present invention to self-assemble into larger structures. The interaction mediated by the tail can be non-specific or specific, and can be used to make a surface or a larger structure mimic the characteristic of fibronectin to bind $\alpha_5\beta_1$ integrin. A tail can include a biodegradable component, can be entirely biodegradable, or can be non-biodegradable.

In one aspect, the tail can be a group allowing a specific interaction between the tail and another molecule. For instance, the tail can include a cysteine residue at the end, which mediates the binding of a compound of the present invention to gold molecules present on a surface. In another example, the tail can include an affinity label such as a biotin or an avidin/streptavidin molecule, which mediates the binding of a compound of the present invention to avidin/streptavidin or to biotin, respectively, present on a surface. Other molecules useful to bind a compound of the present invention to a surface are well known and readily available. Use of a tail allowing a specific or nonspecific interaction between the tail and another molecule permits a compound of the present invention to coat any surface, such as glass, hydrophobic substrates, hydrophilic substrates (such as a hydrogel) or a scaffold of, for instance, non-woven mesh, foam, hydrogel, or sponge.

In another aspect, the tail can be a group allowing a compound of the present invention to interact non-specifically with other molecules, including itself. For instance, the tail can be a hydrophilic group, often referred to in the art as a hydrophilic polymer. Examples of hydrophilic molecules include but are not limited to polyethylene glycol (PEG), polypropylene glycol (PPG), polyoxyethylene (POE), polyethylene oxide (PEO), polytrimethylene glycol, polylactic acid and its derivatives, polyacrylic acid and its derivatives, polyamino acid, polyoxazolidine, polyurethane, polyphosphazene, poly(L-lysine), polyalkylene oxide (PAO), polysaccharide, dextran, polyvinyl pyrrolidone, polyvinyl alcohol (PVA), polyacrylamide, and other polymers. The hydrophilic molecule can be present in a lipid, or a polymer, including homopolymers or heteropolymers (such as copolymers, terpolymers, tetrapolymers, etc.), and may be random, alternating, block, star block, segmented copolymers, or combinations thereof. Hydrophilic molecules are often useful for making scaffolds, such as hydrogels, and use of a compound of the present invention containing a hydrophilic molecule attached to the headgroup can result in a scaffold covered with the headgroup.

Another type of group allowing a compound of the present invention to interact non-specifically with other molecules, including itself, is a hydrophobic molecule. The use of a hydrophobic molecule as a tail results in a amphiphile when bound to a hydrophilic headgroup of the present invention. An amphiphile is a compound with a hydrophobic domain and a hydrophilic domain. A hydrophobic molecule useful as a tail can be any molecule having at least one organic group (preferably, a linear chain) that is capable of forming lipid-like structures. For instance, the organic group may be an alkyl (i.e., saturated), and optionally may be unsaturated (e.g., contain at least one alkyne, at least one alkene, or a combination thereof). The organic group may be a dialkyl, and optionally one or both chains may be unsaturated, or may be a trialkyl. If unsaturated, the organic group may be polymerizable. Suitable hydrophobic molecules can be derived from compounds such as, for example, alcohols (for example, hexadecanol or octadecanol), dialkylamines, dialkylesters, and phospholipids. Examples of naturally occurring compounds from which such hydrophobic molecules can be derived include fatty acids, fatty alcohols, cholesterol, mono-glycerides, diglycerides, phospholipids, cephalins, glycolipids, cerebrosides, cardiolipin, and sphingomyelin. A preferred hydrophobic molecule has one or two $C_{10}$-$C_{22}$ alkyl chains, which are attached to the headgroup or spacer through a linker, such as a trifunctional amino acid. The linker, for example, can be glutamic acid or aspartic acid. Hydrophobic molecules are often useful for making a surface hydrophobic, and use of a compound of the present invention containing a hydrophobic molecule attached to the headgroup can result, for example, in a membrane, vesicle, micelle, or nanofiber covered with the headgroup.

Another type of tail that can be used is an amphiphile. Typically, the headgroup is attached to a hydrophilic domain of the amphiphile. Various amphiphiles are well known in the art and used routinely. The use of a hydrophobic molecule as a tail to make an amphiphile, and the use of an amphiphile as a tail, often permits self assembly, and thus permits the production of, for instance, fibers, including nanofibers (see, for instance, Stupp et al., U.S. Pat. No. 5,932,539, and Hartgerink et al., *Proc. Natl. Acad. Sci. USA,* 2002, 9:5133-5138), micelles, membranes, and vesicles such as liposomes and polymersomes (see, for instance, Discher et al., U.S. Patent Publication 20050048110).

Optionally, and preferably, a tail also includes a structure referred to as a spacer. This structure is typically present between the tail and the headgroup, and can be in combination with the spacer described above. Thus, a compound can have the structure tail-spacer-headgroup, where the spacer is considered to be part of the tail or the headgroup, or can have the structure tail-spacer-spacer-headgroup, where one spacer is considered to the part of the tail and the other spacer is considered to be part of the headgroup. Whether a spacer is considered to be part of a headgroup or a tail is not intended to be limiting in any way, and merely reflects whether the spacer was produced with the headgroup or with the tail. A spacer is any structure that is present between the tail and the headgroup and acts to move the headgroup further from the tail. A spacer may also function to provide greater flexibility of the headgroup with respect to the tail. A spacer may be, for instance, amino acids or an organic group. A spacer can be hydrophilic or hydrophobic, can have a positive charge, negative charge, can be neutral, or a combination thereof. In some aspects, a spacer may be selected based on the ability to make the headgroup more soluble. In some aspects, a spacer may include one or more cysteine residues, which when oxidized may form disulfide bonds to polymerize a self-assembled structure. A space may be, for instance, at least 8 Å, preferably, at least 9 Å, more preferably, at least 10 Å, most preferably, at least 11 Å. Exemplary spacers include lysine-serine-serine and succinic anhydride.

A tail may include suitable functional groups for attachment to the headgroup or spacer. For instance, the tail may be attached to the headgroup or the spacer through a linker group having suitable functionality such as ester groups, amide groups, and combinations thereof. Such a linker is useful for connecting multiple tails (for instance, a dialkyl organic group), or for providing appropriate chemistry to facilitate joining a tail to a headgroup or a spacer.

A compound of the present invention is biologically active. As used herein, the term "biologically active" refers to the ability of a compound of the present invention to bind $\alpha_5\beta_1$ integrins. A compound of the present invention may also influence the behavior of a cell. For example, when a compound of the present invention is present on a surface, the binding of a cell to the surface can result in cell spreading, production of extracellular fibronectin by the cell, network formation within the cell, or a combination thereof. In another example of a compound of the present invention influencing the behavior of a cell, when the compound of the present invention is present on the surface of a vesicle, binding of the vesicle to $\alpha_5\beta_1$ integrins on the cell can result in internalization of the vesicle by the cell.

Whether a candidate compound binds asp, integrins can be determined by measuring the ability of cells expressing the $\alpha_5\beta_1$ integrin to bind to a surface covered with the compound. A candidate compound is a compound having a structure as described herein and being evaluated for its biological activity (e.g., ability to bind $\alpha_5\beta_1$ integrin). For instance, when the candidate compound is an amphiphile, the self assembling character of the candidate compound can be used to produce a membrane having the headgroup present on one side. Preferably, the candidate compound is used to produce supported bilayer membranes, and such membranes can be made using vesicle adsorption and spreading on a surface or the Langmuir-Blodgett (LB) technique. Methods for producing such membranes are well known and used routinely (see, for instance, Kokkoli et al., *Langmuir,* 2004, 20:2397-2404). Briefly, for the LB a commercially available system is used to make LB films, such as those available from KVS Instruments (Helsinki, Finland). Depositions are done at a surface pressure below the 60 mN/m collapse pressure, such as 31-45 mN/m, and the deposition speed for up and down strokes can be between 0.8 mm/minute and 1.2 mm/minute, preferably 1 mm/minute. The first step is typically making the mica, glass, or any other hydrophilic substrate hydrophobic with a layer of 1,2-distearoyl-sn-glycero-3-phosphatidylethanolamine (DSPE) in the upstroke. Other alternative methods for making a surface hydrophobic include, for example, adsorbing hydrophobic molecules, such as, for example, alkanes or silanes. The second layer with the amphiphile is deposited in the down stroke. The resulting supported bilayer membranes may be transferred to glass vials under water, and care is taken to avoid exposing the surfaces to air. The amount of candidate compound present on the surface can be varied, and during initial tests a candidate compound is typically used to fully cover a surface. The concentration of a candidate compound on an LB surface can be altered by mixing it with other lipids, lipidated-PEG, or other peptide-amphiphiles.

Shortly before an assay, the LB membranes are typically transferred to tissue culture plates, e.g., 24-well plates containing phosphate buffered solution. After equilibration, 1 ml of basal media, for instance, MCDB-131, supplemented with 0.1% bovine serum albumin (BSA) and antibiotics (Sigma) (2.5 µg/ml gentamicin, 2.5 µg/ml amphotericin B, 50 U/ml penicillin, and 50 µg/ml streptomycin) is added. Preferably, the media has no serum added. Human fibronectin (FN)-coated coverslips can be used as a positive control, and a suitable negative control is a compound identical to the tail of the candidate compound, but having the peptide GRGESP (SEQ ID NO:6) as the headgroup.

Cells expressing $\alpha_5\beta_1$ integrin can then be added to the surfaces. Cells that express the $\alpha_5\beta_1$ integrin are well known and readily available. An example of a suitable cell is a human umbilical vein endothelial cell (HUVEC), which is commercially available from Cambrex Corp. (East Rutherford, N.J.). Typically, the cells are grown in culture prior to use, and when reaching 80% to 95% confluency are washed, removed from the surface of the tissue culture dish, typically by trypsin-EDTA, washed, and suspended in the same media as the LB and FN surfaces. The cells are added to the surfaces, for instance, at a density of 400 to 600 cell/mm$^2$, preferably, 500 cell/mm$^2$, and incubated for 1 to 12 hours, or more. After washing, the number of cells bound per unit area, for instance, per mm$^2$, to each type of surface can be determined by routine methods. Examples include the use of dyes that bind cellular nucleic acids (CyQuant Cell Proliferation Assay Kit, available from Molecular Probes). A candidate compound is considered to bind $\alpha_5\beta_1$ integrin when the number of cells bound to the compound is greater (at a statistically significant level) than the number of cells bound to a surface coated with a compound having the same tail as the candidate compound and having GRGESP (SEQ ID NO:6) as the headgroup. Preferably, the number of cells binding to a candidate compound is greater (at a statistically significant level) than or equal to the number of cells bound to a fibronectin-coated surface, and/or greater (at a statistically significant level) than a surface coated with a compound having the same tail as the candidate compound and having RGD or GRGDSP as the headgroup.

Preferably, a compound of the present invention specifically binds $\alpha_5\beta_1$ integrins. Whether a candidate compound specifically binds an $\alpha_5\beta_1$ integrin can be determined by including antibodies directed to integrins, including cup, integrin, the $\alpha_5$-subunit, and/or the $\beta_1$-subunit. Antibodies that specifically bind $\alpha_5\beta_1$ integrin, the $C\alpha_5$-subunit, and the $\beta_1$-subunit are well known in the art and commercially available. Antibodies that bind to other integrins and other integrin subunits can be used as controls. Examples include the mouse anti-human monoclonal antibodies P1D6 (anti-integrin subunit C P5D2 (anti-integrin subunit $\beta_1$), JBS5 (anti-integrin $\alpha_5\beta_1$) and LM609 (anti-integrin $\alpha_v\beta_3$) (available from Chemicon Int.). Cells can be blocked by mixing the cell suspension with the appropriate antibody in 0.1% BSA media, and incubating for 30 minutes at 37° C., 5% $CO_2$ with constant agitation. The blocked cells can then be released onto LB and FN surfaces that were earlier transferred to 24- or 12-well plates and pre-incubated in 0.1% BSA media. The cells are allowed to adhere for 30 minutes to 1.5 hours, preferably, 1 hour at 37° C., 5% $CO_2$. Cells can be seeded at any concentration, but decreased numbers of cells permits use of less antibody. For instance, cells can be seeded at 200 to 300 cells/mm$^2$, preferably 250 cells/mm$^2$, with a final antibody concentration in each well of 20 μg/ml. Following incubation, surfaces are washed, and adhered cells are quantified. A candidate compound is considered to specifically bind $\alpha_5\beta_1$ integrin if antibodies to the $\alpha_5\beta_1$ integrin, the $\alpha_5$-subunit, and/or the $\beta_1$-subunit result in a statistically significant decrease in binding of cells to the candidate compound compared to antibodies to other integrins or other integrin subunits.

Whether a cell spreads on a surface that is coated with a candidate compound and produces fibronectin can be determined using the same procedure described above for measuring binding. Briefly, the surfaces are prepared as described above, and after incubation times of 1, 12, 24, 48, and 72 hours the surfaces are washed and fixed in a general fixative, such as paraformaldehyde. The presence of secreted fibronectin can be visualized with an antibody that is specific for secreted fibronectin. Several such antibodies are well known and commercially available (for instance P1H11 from Chemicon Int.). Optionally, a secondary antibody labeled with a detectable label can be used to detect the primary antibody, such as bound anti-fibronectin antibody. The methods used to incubate the primary antibody, and optionally the secondary antibody, are well known in the art and can be determined without the need for undue experimentation. The spreading of the cells can be measured by staining the plasma membrane present in the cell, and methods for accomplishing this are well known in the art, routine, and commercially available from various companies, such as Molecular Probes. Fibronectin production can be assessed visually, by comparing multiple images from different samples. Preferably, a candidate compound that binds $\alpha_5\beta_1$ integrin causes a bound cell to produce fibronectin in an amount that is comparable or greater than the amount of fibronectin secreted by the same cell bound to a surface coated with fibronectin. Cell spreading can be determined by measuring the cell area of multiple images from different samples. Computer algorithms for measuring area are available (for instance, the NIH imaging software).

Whether cytoskeletal organization and focal adhesions of a cell are altered in response to binding to a surface coated with a candidate compound can be determined using the same procedure described above for measuring binding. Briefly, the surfaces are prepared as described above, and after incubation times of 1, 12, 24, 48, and 72 hours the surfaces are washed and fixed in a general fixative, such as paraformaldehyde, and the cells are treated to permit visualization of molecules that make up focal adhesions and the cytoskeleton, such as actin stress fibers, nuclei, and vinculin. The presence of these can be visualized with an antibody or other compounds that specifically bind the intended target. For instance, phalloidin can be used to bind actin, and DAP1 can be used to bind DNA. Preferably, a candidate compound that binds $\alpha_5\beta_1$ integrin causes a bound cell to display actin stress fibers and focal contacts for 1-72 hours. Preferably, a cell bound to a candidate compound assembles longer and thinner vinculin-positive focal adhesion complexes with sharp spikes of vinculin at the termination points and across the actin stress fibers than compared to the cell bound to fibronectin. Preferably, a cell bound to a candidate compound also displays more pronounced actin cytoskeletal organization as elongated stress fibers than the cell bound to fibronectin.

The present invention also provides compositions that include the compounds described herein. In one aspect, the composition includes a compound of the present invention and a surface, where the compound is attached to the surface. The attachment may be non-covalent, for instance, an ionic bond, a hydrogen bond, a Van der Waals force, or a combination thereof, or the attachment may be covalent. For example, a compound can include an avidin molecule and be attached to a surface that includes biotin, or a compound can include a polymer tail that interacts non-specifically with other polymers present oil a surface. The compound may be present on a surface at a concentration of at least 0.5 mol %, at least 1.0 mol %, at least 1.5 mol %, at least 2.0 mol %, or at least 2.2 mol %. The compound may be present on a surface at a concentration of no greater than 5.0 mol %, no greater than 4.5 mol %, no greater than 4.0 mol %, no greater than 3.5 mol %, no greater than 3.0 mol %, or no greater than 2.6 mol %. Methods for determining the concentration of the compound are well known in the art and used routinely, and include, for instance, protein assays such as the BCA assay. A composition of the present invention may include a pharmaceutically acceptable carrier.

A surface can be 2-dimensional, such as a glass coverslip, a Langmuir-Blodgett membrane, or a plastic well in a tissue culture dish, or a surface can be part of a 3-dimensional structure. Examples of such structures include, but are not limited to, vesicles, such as liposomes, polymersomes, and particles, such as nanoparticles (including gold nanoparticles and iron oxide nanoparticles) and microparticles. Particles may optionally be solid and not include a compartment.

Examples of such structures include, but are not limited to, structures that can be used as supports for 3-dimensional tissue formation. A surface may be porous and have an adequate pore size to permit the migration of cells into the structure. A surface may have varied shapes such as, for example, a tubular or cylindrical shape. Three-dimensional structures are often referred to in the art as scaffolds. The present invention also includes such surfaces, including scaffolds.

Examples of scaffolds include, for example, non-woven mesh, foam, hydrogel, sponge, and fibers, such as nanofibers. They can be natural or synthetic, and biodegradable or permanent. A scaffold can be made so that a compound of the present invention is attached to the surface of the structure during production of the structure, or added to the surface after production of the structure. Methods for attaching compounds to the surface of scaffolds are known to the skilled person and used routinely. Scaffolds of the present invention may include additional agents such as, for instance, growth factors, enzymes, and/or hormones.

The composition may include a compound of the present invention attached to the surface of a vesicle. Examples of vesicles include, but are not limited to, liposomes, polymersomes, and particles, such as nanoparticles and microparticles. A vesicle typically includes an interior compartment. Vesicles may include a lipid layer, a compartment surrounded by the lipid layer, and a compound of the present invention attached to the surface of the vesicle. Optionally, a compound of the present invention attached to the surface on the interior of the vesicle as well. The lipid layer may be a bilayer. A compound of the present invention may be present on the surface of a vesicle by being attached to a hydrophobic molecule, e.g., a tail, that is part of the lipid layer. The present invention also includes such vesicles and particles.

Vesicles useful herein may be polymerized, non-polymerized, or hybrid. Polymerized vesicles include polymerizable organic groups (for instance, an unsaturated linear chain) that can be covalently bound to other organic groups having the same or similar structure, and some, most, or all of the polymerizable organic groups are covalently bound to each other by intermolecular-interactions. Non-polymerized vesicles include organic groups that are not covalently bound to other organic groups in the lipid layer, and hybrid vesicles include domains of polymerized organic groups and non-polymerized organic groups.

Vesicles may include a variety of organic groups. Generally, the vesicles, such as liposomes, include at least one phospholipid, typically egg phosphatidylcholine, egg phosphatidylglycerol, distearoylphosphatidylcholine, distearoylphosphatidyl glycerol, or combinations thereof. At least one organic group present in the vesicle is attached to the compound of the present invention, where the organic group acts as a tail. The attachment may be covalent or non-covalent, preferably, covalent.

Other phospholipids suitable for formation of vesicles that include a compound of the present invention include, but are not limited to, phosphatidylcholine, phosphatidylglycerol, lecithin, $\beta,\gamma$-dipalmitoyl-$\alpha$-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipil, cerebrosides, dicetylphosphate, dioleoylphosphatidylcholine, dipalmitoylphosphatidylcholine, dipalmitoylphosphatidyl glycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, 1,2-Dipalmitoyl-sn-Glycero-3-Phosphocholine (DPPC), and the like. Non-phosphorus containing organic groups may also be used in the vesicles. These include, for example, stearylamine, docecylamine, acetyl palmitate, cholesterol, fatty acid amides, and the like. Additional organic groups suitable for use in the vesicles are well known to persons of skill in the art and are cited in a variety of well known sources, e.g., McCutcheon's Detergents and Emulsifiers and McCutcheon's Functional Materials, Allured Publishing Co., Ridgewood, N.J.

The vesicles may include other components, including components that provide particular characteristics to a vesicle. The vesicles may include such components in various combinations. Vesicles may be recognized by phagocytic cells of the reticuloendothelial system, and as a result can be removed from the circulatory system and accumulate in the liver and spleen. Extended circulation times of vesicles can be promoted by inclusion of various molecules with the vesicles. For instance, small amounts (<10%) of polymerizable diacyl phosphatidyl inositol can be incorporated into vesicles, (D. Papahadjopolous et al., *Liposomes: Rational Design*, Janoff, A. S. (Ed.), Marcel Dekker, New York, 1999, pp. 1-12), or polyethylene oxide (PEO) or polyethylene glycol (PEG) conjugated organic groups can be incorporated in vesicles (often referred to in the art as stealth liposomes) to achieve long circulation times (T. Ishida et al., *Bioscience Reports*, 2002; 22:197-224; Woodle et al., U.S. Pat. No. 5,013,556). When PEG conjugated organic groups are used, the molecular weight of the PEG may be between at least 750 and no greater than 5000, preferably between at least 750 and no greater than 2000. A PEG molecule may be linked to an organic group by various linkages, including, for instance, a releasable linkage (Zalipsky et al., U.S. Patent Application 20060240009). Examples of useful PEG molecules include, for instance, 1,2-Dipalmitoyl-sn-Glycero-3-Phosphoethanolamine-N-(Methoxy(Polyethylene glycol)-750)-Ammonium Salt) (PEG750) and 1,2-Dipalmitoyl-sn-Glycero-3 Phosphoethanolamine-N-(Methoxy(Polyethylene glycol)-2000)-(Ammonium Salt) (PEG-2000). The concentration of PEG present on the surface of a vesicle is the concentration that results after including at least 0.5 mol % to no greater than 8 mol % of a PEG conjugated organic group in the mixture used to make the vesicles. Preferably, the concentration of PEG present on the surface of a vesicle is the concentration that results after including at least 0.5 mol %, at least 1 mol %, or at least 2 mol % of a PEG conjugated organic group in the mixture used to make the vesicles. Preferably, the concentration of PEG present on the surface of a vesicle is the concentration that results after including no greater than 8 mol %, no greater than 7 mol %, no greater than 6 mol %, or no greater than 5 mol % of a PEG conjugated organic group in the mixture used to make the vesicles. Optionally, when PEG is present on the surface of a vesicle, the combined total concentration of PEG and the compound of the present invention are not so great that it results in a destabilization of the vesicle membrane. For instance, the combined total concentration of PEG and the compound of the present invention are not greater than 8 mol %.

Vesicles may include components that promote fusion of the vesicle with a cell membrane. For instance, fusogenic vesicles may include a hydrophobic segment extending from the surface of a vesicle for penetration into a cell membrane (Martin et al., U.S. Pat. No. 5,891,468). Other fusion-promoting molecules are well known in the art and used routinely, and include, for instance, fusion peptides that mimic portions of viruses.

Vesicles may also include components that can promote the destabilization of the vesicle lipid membrane and release of the vesicle contents when the vesicle encounters certain conditions. Such conditions include triggers such as, for instance, change in pH, mechanical stress, metal ions, temperature, ultrasound, light, alkaline phosphatase, and phospholipase $A_2$. Preferably, vesicles including a compound of the present invention are stable at physiological pH (pH 7.6 to pH 7.2, but become less stable as the pH decreases. For instance, a vesicle that is sensitive to a pH trigger can begin to release its contents when the pH of the solution surrounding the vesicle decreases to no greater than 7.0, no greater than 6.5, no greater than 6.0, or no greater than 5.5. Components that can be used to make vesicles sensitive to external triggers are well known in the art and used routinely. For example, vesicles sensitive to a pH trigger may include an organic group such as dioleoylphosphatidylethanolmaine (DOPE) (see, for instance, Simoes et al., *Adv. Drug Deliv. Rev.*, 2004; 56(7):947-965). Optionally, such organic groups may be stabilized in the bilayer state by inclusion of other components, for instance, cholesteryl hemisuccinate (CHEMS), or an amphipathic lipid having a bulky hydrophobic moiety, such as PEG (Zalipsky et al., U.S. Patent Application 20060240009).

Vesicles typically have a spherical structure that encapsulates an interior compartment. This interior compartment typically includes an aqueous liquid, and there may be one or more agents present in the liquid. The agent may be, for instance, a liquid, a solid that is dissolved in the liquid, a solid that is suspended in the liquid, or a lipophilic agent that stably partitions in the lipid phase of the vesicle. Examples of agents include, but are not limited to, small, water-soluble organic compounds, proteins, DNA plasmids, oligonucleotides (including antisense, siRNA, and ribozymes) and polynucleotides encoding a protein. An agent may be therapeutic (e.g., able to treat or prevent a disease) or non-therapeutic (e.g., not directed to the treatment or prevention of a disease). Examples of therapeutic agents include, for instance, chemotherapeutic agents, enzyme inhibitors, and oligonucleotides. Examples of non-therapeutic agents include, for instance, imaging agents for tracking progression of a disease, or for use in in vitro diagnostic assays. Imaging agents include, for example, chelates of radionuclides, enzymes, or fluorophores. In some aspects, the liquid preferably includes a pharmaceutically acceptable carrier. "Pharmaceutically acceptable" refers to a diluent, carrier, excipient, salt, etc., that is compatible with pharmaceutical administration and not deleterious to a recipient thereof.

Compounds of the present invention can be made by a variety of solid-phase or solution techniques. For example, although the headgroup can be prepared by other methods (e.g., solution methods) and then attached to a support material for subsequent coupling with the tail or spacer, it is preferred that standard solid-phase organic synthesis techniques, such as solid-phase peptide synthesis (SPPS) techniques be used. That is, a peptide can be synthesized, if desired, subsequently attached to a support material, coupled with a tail or spacer, and then removed from the support material using a variety of techniques.

For the preparation of a headgroup, solid-phase peptide synthesis may involve a covalent attachment step (i.e., anchoring) that links the nascent peptide chain to a support material (typically, an insoluble polymeric support) containing appropriate functional groups for attachment. Subsequently, the anchored peptide is extended by a series of addition (deprotection/coupling) cycles that involve adding $N^\alpha$-protected and side-chain-protected amino acids stepwise in the C to N direction. Once chain assembly has been accomplished, protecting groups are removed and the headgroup is cleaved from the support. Typically, if a tail or spacer is to be added, the tail or spacer is added to the headgroup before the protecting groups are removed and the peptide is cleaved from the support.

When solid-phase peptide synthesis techniques are used to synthesize the peptides on the support material, Fmoc methodologies are preferably used. The Fmoc group can be removed using piperidine in dimethylformamide (DMF) or N-methylpyrrolidone, or using 1,8-diazabicyclo[5.4.0]undec-7-ene (DBU) in DMF. After Fmoc removal, the liberated $N^\alpha$-amine of the supported resin is free and ready for immediate attachment of the lipid without an intervening neutralization step. At the end, amino acid deprotection and resin cleavage can be accomplished using 5% $H_2O$ in trifluoroacetic acid (TFA) or Reagent K at room temperature. Such Fmoc solid-phase peptide synthesis methodologies are well known to one of skill in the art and are discussed in Fields et al., *In Synthetic Peptides: A User's Guide*, 1992, G. A. Grant, Ed., Chapter 3, pp. 77-183, W.H. Freeman and Co., N.Y.; Fields et al., *Int. J. Peptide Protein Res.*, 1990; 35:161-214; and Berndt et al., *J. Am. Chem. Soc.*, 1995; 117:9515-9522. Peptides, to be used in the compounds of the present invention, including peptides on a support material, can also be obtained commercially.

For preparation of a tail, the molecules described herein can be obtained commercially or made using routine and well known methods, and routine and well known methods can be used to couple a tail to a headgroup.

Scaffolds can be made from any type of polymer, ceramic, metal, or mixture of any type suitable for adhering cells thereto. Examples of synthetic polymers include, but are not limited to, aliphatic polyesters such as polyglycolic acid (PGA), polylactic acid (PLLA), their copolymers (e.g. PLGA) polymethylcaprolactone, and polycaprolactone (Griffith, *Acta. Mater.*, 2000, 48:263-277; Freed et al., *Adv. Drug Deliver. Rev.*, 1998; 33: 15-30; Agrawal et al., *J. Biomed. Mater. Res.*, 2001; 55:141-150; Hutmacher, *J. Biomat. Sci.-Polym.*, 2001; E 12:107-124). Examples of natural polymers are typically polysaccharides, polypeptides, and/or polyesters. Exemplary polysaccharides include, for instance, plant polysaccharides (e.g., algal polysaccharides such as alginate, galactans, carrageenans, and exudate gums such as gum arabic), animal polysaccharides (e.g., chitin, chitosan, glycosaminoglycans, hyaluronic acid), and microbial polysaccharides (e.g., dextran, gellan gum, pullulan, xanthan gum, and cellulose). Examples of naturally derived polyesters include polyhydroxylalkanoates, such as poly (hydroxybutyrate) and poly(hydroxybutyrate-co-valerate). Examples of ceramic materials include, for instance, hydroxyapatite and tricalcium phosphate. Amphiphilic molecules such as peptide-amphiphiles attached to synthetic tails or polymers can be used for the self-assembly and formation of nanofibers and gels.

Several methods for making scaffolds have been developed, and are well known to the skilled person and used routinely. Such methods include, for instance, conventional fabrication techniques and solid freeform fabrication techniques (Sachlos et al., Europ. *Cells Materials*, 2003; 5:29-40, Mano et al., *J. R. Soc. Interface*, 2007). Examples of conventional fabrication techniques include solvent-casting particulate-leaching, gas foaming, fiber meshes/fiber bonding, phase separation, melt moulding, emulsion freeze drying, solution casting, and freeze drying. Examples of solid freeform fabrication techniques include three dimensional printing, stereolithography, fused deposition modelling, 3D plotting and phase-change jet printing. Other methods of making scaffolds include self-assembly (see, for instance, Stupp et al., U.S. Pat. No. 5,932,539, and Hartgerink et al., *Proc. Natl. Acad. Sci. USA*, 2002; 99:5133-5138).

Methods for making vesicles are well known and used routinely. Suitable methods include, e.g., sonication, extrusion, high pressure/homogenization, microfluidization, detergent dialysis, calcium-induced fusion of small liposome vesicles, and ether-infusion methods, all well known in the art. See, for instance, Steck et al., (U.S. Pat. No. 4,186,183), Vanlerberghe et al., (U.S. Pat. No. 4,217,344), Mezei et al., (U.S. Pat. No. 4,485,054), Fidler (U.S. Pat. No. 4,774,085), Hong et al., (U.S. Patent Application 20070116753), Discher et al., (U.S. Patent Application 20050048110), Hope et al., (U.S. Pat. No. 7,101,570), Zalipsky et al., (U.S. Patent Application 20060240009), Singh (U.S. Pat. No. 5,366,881), and Brey et al., (U.S. Pat. No. 6,500,453).

Methods for functionalizing a surface with a molecule are well known and used routinely, and can be used to functionalize a surface with a compound of the present invention. A functionalized surface refers to a surface that includes a compound of the present invention on its surface. The presence of the compound on the surface can result in the surface having one or more of the biological activities described herein. Typically, a compound of the present invention is produced with a tail that permits the attached compound to interact with molecule(s) present on a surface, and non-limiting examples of useful tails are discussed hereinabove. The production of surfaces, for instance, scaffolds and vesicles, that have characteristics suitable for adding a compound of the present invention are well known and used routinely. For instance, a surface can be produced that has biotin on the surface and the tail of a compound can be avidin, or a compound of the present invention can be produced with a hydrophobic tail and used to make a vesicle, such as a liposome, that includes the compound on the surface.

A composition of the present invention may be formulated to be compatible with its intended route of administration. For instance, scaffolds may be formulated as a shape-retaining solid, either molded or moldable to a shape suitable for contact with a damaged or diseased tissue, or it can be in the form of a paste or putty which can be pressed into the tissue defect site by surgeon at the time of implant to take the shape of the defect. Alternatively, a scaffold composition can be prepared in the form of an injectable gel or liquid. Typically, such a gel or liquid has a phase transition temperature permitting injection as a liquid or a gel above body temperature, and undergoing phase change to crystalline or semi-crystalline form at body temperature. Vesicles intended for intravenous administration may be formulated as a sterile solution with an appropriate carrier.

Examples of routes of administration include perfusion and parenteral, e.g., intravenous, intradermal, subcutaneous, oral (e.g., inhalation), transdermal (topical), transmucosal, and rectal administration (e.g., retention enema or suppository). In formulations of compositions of the present invention, wetting agents, emulsifiers and lubricants, such as sodium lauryl sulfate and magnesium stearate, as well as coloring agents, release agents, coating agents, sweetening agents, flavoring agents, preservatives and antioxidants may be present.

Formulations can include sterile aqueous solutions or dispersions and sterile powders for the extemporaneous preparation of sterile solutions or dispersions. For intravenous administration, suitable carriers include, for instance, physiological saline, bacteriostatic water, or phosphate buffered saline (PBS). A composition is typically sterile and, when suitable for injectable use, should be fluid to the extent that easy syringability exists. It should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Methods of preparing these formulations or compositions include the step of bringing into association a composition of the present invention, with the carrier and, optionally, one or more accessory ingredients. In general, the formulations are prepared by uniformly and intimately bringing into association a composition of the present invention with liquid carriers, or finely divided solid carriers, or both, and then, if necessary, shaping the product.

Oral compositions generally include an inert diluent, an edible carrier, or the combination. For the purpose of oral therapeutic administration, a composition of the present invention can be incorporated with excipients and used in the form of tablets, troches, or capsules, e.g., gelatin capsules. Pharmaceutically compatible binding agents, and/or adjuvant materials can be included as part of the formulation. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, a composition of the present invention may be delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

A composition of the present invention can also be prepared in the form of suppositories (e.g., with conventional suppository bases such as cocoa butter and other glycerides) or retention enemas for rectal delivery.

The compounds described herein provide a simple and general approach for modifying surfaces to have the activity of binding, preferably specifically binding, $\alpha_5\beta_1$ integrins. The compounds described herein have the advantage of providing surfaces that bind $\alpha_5\beta_1$ integrins better than surfaces coated with fibronectin. This typically results in improved interaction of such a surface with cells and tissues, including greater cell adhesion, better cytoskeletal organization, greater production of ECM, and greater cell spreading, all of which result in the advantage of promoting viability of cells. In other aspects, a vesicle with a compound of the present invention can targeted to cells expressing $\alpha_5\beta_1$ integrins and result in the advantage of being internalized by the cells.

Scaffolds modified to include compounds of the present invention can be used for implantation into patients. Such scaffolds can be used for regeneration of tissues, or to replace organs that are malfunctioning or failing. For example, scaffolds can be combined with viable cells to serve as a temporary matrix for cell growth and concomitant regeneration of tissue at an implant site. For instance, scaffolds can be used for cartilage regeneration, bone regeneration, skin substitution, cardiovascular tissue regeneration, knee ligament, and artificial organs such as liver, pancreas, and bladder. The surfaces of scaffolds that are known to the skilled person and used routinely can be easily modified to include compounds of the present invention. The present invention includes methods for using scaffolds for, e.g., wound healing and angiogenesis.

The present invention is further directed to methods for using the vesicles and/or particles of the present invention. In one aspect, the methods of the present invention include contacting a membrane with a structure having a compound of the present invention attached to the surface, such as a vesicle or a particle. The membrane can be an artificial membrane (e.g., a Langmuir-Blodgett membrane), or part of a cell. The membrane typically includes $\alpha_5\beta_1$ integrins on the surface. The cell membrane can be present in conditions suitable for the internalization of the vesicle by the cell, or the contacting can be followed by exposing the cell and vesicle to conditions suitable for the internalization of the vesicle by the cell. The internalization can be active or passive. The cell is typically vertebrate, and preferably mammalian, such as human, or a member of the family Muridae (a murine animal such as rat or mouse). The cell can be ex vivo or in vivo. As used herein, the term "ex vivo" refers to a cell that has been removed from the body of a subject. Ex vivo cells include, for instance, primary cells (e.g., cells that have recently been removed from a subject and are capable of limited growth in tissue culture medium), and cultured cells (e.g., cells that are capable of extended culture in tissue culture medium). As used herein, the term "in vivo" refers to a cell that is within the body of a subject. Suitable cells are those that have $\alpha_5\beta_1$ integrin present on their surface. Examples of readily available cells expressing $\alpha_5\beta_1$ integrin include, for instance, human umbilical vein endothelial cells, mouse colon cancer cells such as CT26.WT cells (ATCC No. CRL-2638), human colon cancer cells such as HCT116 (ATCC No. CRL-247) and RKO (ATCC No. CRL-2577), and derivatives thereof. Primary cells such as breast, colon, rectal, and prostate cancer cells can be obtained from tumors.

If a cell membrane is contacted with a vesicle under suitable conditions, the vesicle and/or particle may be internalized. Conditions that are "suitable" for an event to occur, such as internalization, spreading by a cell, production of extracellular fibronectin by cell, or network formation within a cell, are conditions that do not prevent such events from occurring. Thus, these conditions permit enhance, facilitate, and/or are conducive to the event. Such conditions, known in the art and/or described herein, may depend upon, for example, the temperature of the components, or media conditions, such as the presence or absence of serum. A vesicle may be actively internalized by a cell, for instance, by endocytosis, or passively internalized. Typically, passive internalization is mediated by a component that promotes fusion of the vesicle with a cell membrane.

When contacting a cell membrane with a vesicle and/or particle includes, or is followed by, conditions suitable for the internalization of the vesicle and/or particle by the cell, the methods may be used for introducing an agent into a cell. Introducing an agent that is non-therapeutic may be used to deliver agents useful for imaging and/or diagnostic assays, thus the invention includes methods for identifying cells expressing $\alpha_5\beta_1$ integrins, such as, for instance, whole tumors. The methods for delivering agents useful for imaging and/or diagnostic assays typically include administering to a subject in need thereof a composition including an effective amount of a vesicle of the present invention, where the vesicle includes an appropriate agent. Optionally, the method further includes identifying the agent in a cell. The cell may be ex vivo or in vivo. An "effective amount" is an amount effective to elicit the desired result. In this aspect, an effective amount is the amount effect to permit the imaging or diagnosis to occur. Preferred methods for administering a vesicle of the present invention include administration by methods known in the art including, for instance, intravenous administration.

Introducing an agent that is therapeutic may be used to deliver agents useful for treating a disease, thus, the present invention also includes methods for treating certain diseases in a subject. The subject is a mammal, preferably a human. As used herein, the term "disease" refers to any deviation from or interruption of the normal structure or function of a part, organ, or system, or combination thereof, of a subject that is manifested by a characteristic symptom or set of symptoms. Diseases include, but are not limited to, cancers that include cancerous cells expressing the $\alpha_5\beta_1$ integrin on their surface. Examples of such diseases are referred to as $\alpha_5\beta_1$ integrin positive cancers, and include, but are not limited to, breast, colon, rectal and prostate cancer. Typically, whether a subject has a disease, and whether a subject is responding to treatment, is determined by evaluation of symptoms associated with the disease. As used herein, the term "symptom" refers to objective evidence of a disease present in a subject. Symptoms associated with diseases referred to herein and the evaluation of such symptoms are routine and known in the art. Examples of symptoms of cancers include, for instance, the presence and size of tumors, and the presence and amount of biomarkers. Biomarkers are compounds, typically polypeptides, present in a subject and indicative of the progression of cancer. An example of a biomarker is prostate specific antigen (PSA).

Treatment of a disease can be prophylactic or, alternatively, can be initiated after the development of a disease. Treatment that is prophylactic, for instance, initiated before a subject manifests symptoms of a disease, is referred to herein as treatment of a subject that is "at risk" of developing a disease. An example of a subject that is at risk of developing a disease is a person having a risk factor, such as a genetic marker, that is associated with the disease. Examples of genetic markers indicating a subject has a predisposition to develop certain cancers such as breast, prostate, or colon cancer include alterations in the BRAC1 and/or BRAC2 genes. Treatment can be performed before, during, or after the occurrence of the diseases described herein. Treatment initiated after the development of a disease may result in decreasing the severity of the symptoms of one of the conditions, or completely removing the symptoms.

In some aspects, the methods typically include introducing into a cell an effective amount of an agent, where the agent is delivered to the cell in a vesicle and/or particle of the present invention. An "effective amount" in this aspect is an amount effective to decrease a symptom associated with the disease. The agent can be any therapeutic agent, and many such agents are well known and used routinely. It is expected that use of the vesicles described herein will be permit the use of lower levels of therapeutic agents and result in less of an impact on tissues and cells that do not include $\alpha_5\beta_1$ integrins.

Whether a vesicle and/or particle will function in the methods of the present invention to treat a disease can be evaluated using ex vivo models and animal models. Such models are known in the art and are generally accepted as representative of disease or methods of treating humans. For example, an ex vivo model is the use of cancer cell lines such as CT26.WT, HCT116, and RKO, or primary cells such as colorectal cells. When the cell is ex vivo, the result of delivering a therapeutic agent to a cell can be compared with the same type of cell that is not exposed to the agent. Such a cell that is not exposed to the agent is referred to as a control cell. A decrease in, for instance, survival or replication of the cell exposed to the agent indicates the agent was introduced into the cell.

The study of various cancers in animal models (for instance, mice) is a commonly accepted practice for the study of cancers. For instance, the nude mouse model, where human tumor cells are injected into the animal, is commonly accepted as a general model useful for the study of a wide variety of cancers. Transgenic animal models are also available. For instance, models for the study of prostate cancer such as the TRAMP model (see, for instance, Greenberg et al., *Proc. Natl. Acad. Sci. USA*, 1995; 92:3429-3443) and for breast cancer such as the MMTV-Wnt-1 model (see, for instance, Tsukamoto et al., *Cell*, 1988; 55:619-625) are commonly accepted as models for human disease. A vesicle of the present invention encapsulating an appropriate agent can be used in these animal models to determine if the vesicle delivers the agent to the target cells as expected. Likewise, a vesicle of the present invention encapsulating an appropriate agent can be used in these animal models to determine the agent acts to decrease one or more symptoms associated with the disease.

The methods for treating a subject typically include administering to a subject at risk for a disease or having the disease a composition including an effective amount of a vesicle and/or particle of the present invention, where the vesicle includes an appropriate agent and where a symptom associated with the disease is decreased. Preferred methods for administering a vesicle of the present invention include administration by methods known in the art including, for instance, intravenous administration.

Toxicity and therapeutic efficacy of vesicles of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred.

The data obtained from cell culture assays and animal studies can be used in formulating a range of dosage for use in humans. The dosage of such vesicles and/or particle lies preferably within a range of circulating concentrations that include the $ED_{50}$ with little or no toxicity. The dosage may vary within this range depending upon the dosage form employed and the route of administration utilized. For a vesicles used in the methods of the invention, the therapeutically effective dose can be estimated initially from cell culture assays. A dose may be formulated in animal models to achieve a circulating plasma concentration range that includes the $IC_{50}$ (i.e., the concentration of the test vesicles which achieves a half-maximal inhibition of symptoms) as determined in cell culture. Such information can be used to more accurately determine useful doses in humans. Levels in plasma may be measured, for example, by high performance liquid chromatography. Since the vesicles are able to target specific populations of cells, it is expected that the amount of agent needed to produce the desired effect will be less than what is required when the agent is administered systemically and not encapsulated by a vesicle.

The present invention also provides kits for practicing the methods described herein. The kit includes one or more of the vesicles, particles, or scaffolds of the present invention, or components for the production of such vesicles, particles, or scaffolds, in a suitable packaging material in an amount sufficient for at least one administration. Optionally, other reagents such as buffers and solutions needed to practice the invention are also included. Instructions for use of the packaged vesicles, particles, or scaffolds are also typically included.

As used herein, the phrase "packaging material" refers to one or more physical structures used to house the contents of the kit. The packaging material is constructed by well known methods, preferably to provide a sterile, contaminant-free environment. The packaging material has a label which indicates that the vesicles or scaffolds, or components for the production of such vesicles or scaffolds, can be used for the methods described herein. In addition, the packaging material contains instructions indicating how the materials within the kit are employed to practice the methods. As used herein, the term "package" refers to a solid matrix or material such as glass, plastic, paper, foil, and the like, capable of holding within fixed limits the vesicles, scaffolds, or components for the production of such vesicles or scaffolds. Thus, for example, a package can be a glass vial used to contain appropriate quantities of the vesicles. "Instructions for use" typically include a tangible expression describing the conditions for use of the vesicles, scaffolds, or components for the production of such vesicles or scaffolds.

The present invention is illustrated by the following examples. It is to be understood that the particular examples, materials, amounts, and procedures are to be interpreted broadly in accordance with the scope and spirit of the invention as set forth herein.

Example 1

This example describes engineering biomimetic peptide-amphiphiles that target and increase adhesion with the $\alpha_5\beta_1$ integrin. The design features $C_{16}$ dialkyl ester tails, a glutamic acid (Glu) linker, a —$(CH_2)_2$— spacer, and the peptide headgroup. The headgroup contains two fibronectin-mimicking peptide sequences: fibronectin's primary binding ligand for the $\alpha_5\beta_1$ integrin, RGDSP (natively found in the tenth type III module—FNIII10), and $\alpha_5\beta_1$'s synergy binding ligand, PHSRN. This synergy site in fibronectin type III repeat 9 (FNIII9) consists of about half a dozen amino acids on the side of the domain that is facing RGD (Leahy et al., *Cell*, 1996; 84:155-164; Redick et al., *J. Cell Biol.*, 2000; 149:521-527; Kauf et al., *Biochemistry*, 2001; 40:9159-9166). In native fibronectin, PHSRN and RGD, are separated by 30-40 Å (Leahy et al., *Cell*, 1996; 84: 155-164). Apparently this distance plays a role in the ability of PHSRN to play a synergistic role in adhesion, as studies have shown that incremental extensions of the interdomain link between FNIII9 and FNIII10 reduced cell attachment and affected cell spreading and phosphorylation of focal adhesion kinase (Grant et al., *J. Biol Chem.* 1997; 272:6159-6166).

In the studies presented here, LB membranes on mica substrates constructed from PR_a, PR_b, GRGDSP, and an equimolar mixture of GRGDSP and PHSRN peptide-amphiphiles were used to investigate the effect of different substrates on cell adhesion, spreading, cytoskeletal organization, and fibronectin production. All experiments were conducted in the absence of fetal bovine serum, in order to investigate the effect of the bioactive peptide sequence on these phenomena. LB membranes of GRGESP (SEQ ID NO:6) peptide-amphiphiles were used as a negative control and fibronectin-coated glass slides (referred to as FN) were used as a positive control.

Materials and Methods

Surface preparation: Peptide-amphiphiles, listed in Table 1, were synthesized as described in the literature (Berndt et al., *J. Am. Chem. Soc.*, 1995; 117:9515-9522). Langmuir-Blodgett (LB) membranes constructed from peptide-amphiphiles were deposited onto 15 mm mica disks as described elsewhere (Kokkoli et al., *Langmuir*, 2004; 20:2397-2404). Shortly before cell assays, the LB films were transferred into 24-well plates containing 1× phosphate buffered saline (PBS) solution (Mediatech), without exposing surfaces to air, as they rearrange to form multilayers (Hansma et al., *Method. Cell Biol.*, 2002; 69:163-193). After equilibrating for 5-10 minutes, PBS was exchanged with 1 ml of MCDB-131 basal media (Sigma) supplemented with 0.1% bovine serum albumin (BSA) (Sigma) and antibiotics (Sigma) (2.5 μg/ml gentamicin, 2.5 μg/ml amphotericin B, 50 U/ml penicillin, and 50 μg/ml streptomycin), referred to as 0.1% BSA media. Surfaces were equilibrated at 37° C., 5% $CO_2$ for 30-60 minutes before adding the cells. Human fibronectin-coated round coverslips (FN) 22 mm in diameter (BD Biosciences) were put into 12-well plates and 2 ml of 0.1% BSA media was added to each well. Surfaces were equilibrated for 30-60 minutes at 37° C., 5% $CO_2$.

(P5D2), $\alpha_5\beta_1$ (JBS5), and $\alpha_v\beta_3$ (LM609) monoclonal antibodies (Chemicon Int.). All surfaces were transferred to 24- or 12-well plates and pre-incubated in 0.1% BSA media as described above. HUVECs were prepared and counted as described in the cell adhesion protocol. Cells were blocked by mixing the cell suspension with the appropriate antibody in 0.1% BSA media, and incubating for 30 minutes at 37° C., 5% $CO_2$ with constant agitation. Blocked cells were then released onto LB and FN surfaces and allowed to adhere for 1 hour at 37° C., 5% $CO_2$. For all blocking experiments, cells were seeded at 249 cells/mm$^2$ (lower seeding density was used here to reduce the amount of antibodies needed to block cell adhesion) and a final antibody concentration in each well was 20 μg/ml. Following incubation, surfaces were washed, and adhered cells were quantified as described in the cell adhesion protocol.

Cell spreading and fibronectin production experiments: Surface transferring, cell seeding, and incubation were done in the same manner as in the adhesion experiment, with a cell density of 497 cells/mm$^2$, and incubation times of 1, 12, 24, 48, and 72 hour. At the end of each incubation, the surfaces were removed, washed with 0.10 mil of PBS, and fixed in 1 ml of 4% paraformaldehyde (Sigma) in PBS for 15 minutes at

TABLE 1

Structure and nomenclature of peptide-amphiphiles used in this study.

| Peptide-Amphiphile Structure | Abbreviation | Linker between PHSRN and RGD | Linker Distance (3.7 Å/amino acid[a]) |
|---|---|---|---|
| $(C_{16})_2$-Glu-$C_2$-GRGDSP | GRGDSP | — | |
| $(C_{16})_2$-Glu-$C_2$-GRGESP | GRGESP | — | |
| $(C_{16})_2$-Glu-$C_2$-PHSRN | PHSRN | — | |
| $(C_{16})_2$-Glu-$C_2$-PHSRNSGSGSGSGRGDSP | PR_a | (SG)$_4$ | 29.6 Å |
| $(C_{16})_2$-Glu-$C_2$-KSSPHSRNSGSGSGSGRGDSP | PR_b | (SG)$_5$ | 37 Å |

[a]Idiris et al., Protein Eng., 2000: 13: 763-770; Kokkoli et al., Langmuir, 2004; 20: 2397-2404

Cell culture: Human umbilical vein endothelial cells, HUVECs, (Cambrex Corporation) were cultured in MCDB-131 containing 20% fetal bovine serum (FBS) (Atlas Biologicals) at 37° C., 5% $CO_2$. Other nutrients and antibiotics supplementing the media were added based on an optimal HUVEC proliferation study (Terramani et al., *In Vitro Cell Dev. Biol.—Animal*, 2000; 36:125-132). Media was changed in the culture flasks every other day. Cells used for adhesion and imaging studies were in passages 3-4.

Cell adhesion experiments: After cells became 90% confluent they were washed with PBS, trypsinized with 0.25% Trypsin-EDTA (Cambrex Corporation), neutralized with MCDB-131 with 2% FBS, and spun at 1000 rpm for 10 minutes. The supernatant was removed and the cell pellet was resuspended in 0.1% BSA media. Cells were counted with a hemocytometer and seeded onto LB and FN surfaces at a density of 497 cells/mm$^2$. Surfaces were incubated with cells in 0.1% BSA media at 37° C., 5% $CO_2$, for 1, 4, 12, 24, 48, and 72 hours. Cell adhesion was quantified using the CyQuant Cell Proliferation Assay Kit, with a dye that binds to cellular nucleic acids, following the manufacturer's protocol (Molecular Probes). A calibration standard curve was created for each experiment. The plates were read on a SpectraMAX GeminiXS (Molecular Devices).

Adhesion blocking experiments: Blocking experiments were done using mouse anti-human integrin as (P1D6), $\beta_1$ 37° C., 5% $CO_2$. After washing with PBS, surfaces were first labeled for secreted fibronectin: surfaces were subjected to a blocking solution (0.1% BSA in PBS) for 30 minutes, incubated for 1 hour with a primary antibody specific for secreted fibronectin (mouse anti-human fibronectin (P1H11) monoclonal antibody (Chemicon Int.) at a 1:500 dilution in blocking solution, and then for 45 minutes with a secondary antibody (IgG fluorescein (FITC) conjugated antibody; Chemicon Int.) at a 1:200 dilution in PBS. As a final step, cell membranes and nuclei were stained using the Image-iT™ LIVE Plasma Membrane and Nuclear Labeling Kit following the manufacturer's protocol for labeling fixed cells (Molecular Probes). After final washing, surfaces were mounted onto glass slides and stored at 4° C. protected from light. An inverted fluorescent microscope (Nikon Eclipse TE200 with Pixcell II LCM) was used for imaging. Fibronectin production was assessed visually, by comparing 10-20 fluorescence images from two samples for each substrate (two independent experiments performed at different days). Cell spreading was quantified from two samples per substrate (two independent experiments performed at different days) by measuring cell area with the NIH imaging software.

Actin cytoskeleton and focal adhesion staining: Surface transferring, cell seeding, incubation, and fixing were done as described above. Staining for the actin cytoskeleton, focal adhesions, and nucleus of attached cells was done using the Actin Cytoskeleton and Focal Adhesion Staining Kit following the manufacturer's protocol (Chemicon Int.) and using 1:350 dilution for anti-vinculin antibody, 1:200 for the secondary antibody, approximately 1:1000 dilution (equivalent to 1 unit/surface) for TRITC-conjugated phalloidin and 1:1000 for DAPI. After washing, surfaces were mounted onto glass slides and stored at 4° C. protected from light. A confocal microscope (BIORAD Multiphoton Confocal 1024) was used for imaging.

Results and Discussion

Figure 5:
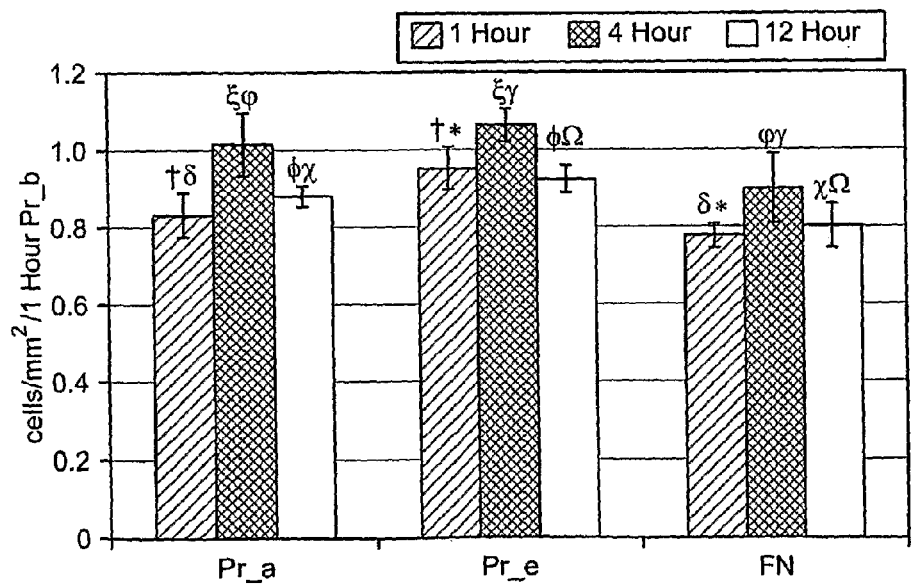
FIG. 5. Effect of linker length on HUVEC adhesion to novel peptides. Cell adhesion was evaluated on LB membranes of Pr_a, Pr_e, and the positive control FN at 1, 4, and 12 hours. HUVECs were incubated at seeding density 497 cells/mm$^2$ on substrates at 37° C., 5% $CO_2$ in the absence of serum. Results are given as the cell density value for each particular surface and time period divided by the cell density value of Pr_b at 1 hour. Matching symbols above any 2 separate columns indicate a p-value given the null hypothesis that the two adhesion densities are the same. z-test analysis for δ, ξ, ᵠ, φ: p<0.7, indicating no statistical difference; z-test analysis for †, γ, χ: p<0.03, indicating a statistically significant difference; z-test analysis for ✽, Ω: p<0.001, indicating very strong evidence of a statistically significant difference. Each histogram represents the mean±SD. For all substrates, n=3 (three independent experiments performed on different days).

Human umbilical vein endothelial cells (HUVECs) were seeded on different substrates (GRGESP, GRGDSP, 50% GRGDSP-50% PHSRN, PR_a, PR_b, and FN) and the cell density was examined after 1, 4, 12, 24, 48, and 72 hours (FIG. 1). For all LB surfaces, a small decrease in cell adhesion was observed after 1 hour of incubation, which could be due to the absence of serum in culture media. Additionally, for all substrates an increase in adhesion was observed going from 4 to 12 hours, which can be attributed to the onset of fibronectin production at 12 hours, as shown in FIG. 5. GRGDSP (SEQ ID NO:7) substrates failed to sustain HUVEC adhesion after 48 hours, as at this point the cell density was similar to the one observed for the inactive GRGESP (SEQ ID NO:6) peptide. The absence of serum in the media, and the minimal amount of fibronectin production on GRGDSP surfaces compared to PR_a, PR_b, and FN, can be possible explanations for the failure of the GRGDSP film. Similarly, substrates functionalized with an equimolar mixture of GRGDSP and PHSRN did not sustain adhesion after 72 hours. Cells effectively adhered to PR_a and PR_b for 72 hours; however, the PR_b peptide-amphiphile was the most promising sequence, comparing favorably to the natural protein ligand, as it gave higher adhesion than FN for 1-24 hours. At 48, and 72 hours cell adhesion was similar on both PR_b and FN surfaces. At this point in time the areas under and around the cells on both PR_b and FN, were fully covered with ECM secreted fibronectin. Thus, the cells were attached to the produced protein, and the substrate that was below the secreted ECM fibronectin did not contribute to the cell attachment.

An increase in cell adhesion on PR_b compared to FN for 1-24 hour may be attributable to a combination of two factors. The first contribution comes from the amino acid sequence of PR_b accurately mimicking the cell binding domain of fibronectin. No previous studies that used saturation levels of fibronectin-mimetic peptides showed such an improved performance compared to fully covered fibronectin surfaces. The second factor was a higher molar concentration of PR_b versus FN, which is an advantage one has in functionalizing an interface with a peptide versus a protein. The coating concentration of FN was 15-35 µg/ml and corresponded to a full monolayer of the protein (information provided by the manufacturer). Experimental studies show that within this range of coating concentrations, the fibronectin surface density is 350-450 ng/cm$^2$ (Garcia et al., *Mol. Biol. Cell*, 1999; 10:785-798). Based on the dimensions of the molecule (60×4 nm) (Williams et al., *J. Biol. Chem.*, 1982; 257:14973-14978), 350 ng/cm$^2$ (0.692 pmoles/cm$^2$) represents the amount of fibronectin necessary to produce a monolayer coating. At the deposition pressure of the experiment, the LB isotherm of PR_b shows an area of 0.51 nm$^2$/molecule, that corresponds to 325 pmoles/cm$^2$. Therefore at saturation conditions, the ratio of PR_b:FN molecules is 470:1.

Cell spreading was evaluated for FN, PR_a, PR_b, GRGDSP, and GRGESP surfaces (FIG. 2). The area of cells seeded on inactive GRGESP surfaces and incubated for up to 24 hours was found to be the smallest and the cells were mostly round (FIG. 2a, b, c). The spreading of attached HUVECs on GRGDSP was higher compared to GRGESP, but much smaller than FN for 1-24 hours (FIG. 2a, b, c). In contrast, cells seeded on PR_a, PR_b, and FN surfaces were mostly spread, however to a different extent depending on the bioactive sequence. It was also noticed that initially, after 1 hour of incubation, cells were evenly distributed throughout the PR_a, PR_b, and FN surfaces, whereas cell clusters were observed at 24 and 48 hour. Adhered cells at 72 hours were again more evenly distributed throughout the PR_a, PR_b, and FN surfaces. For all times examined, cells were found to spread the most on the PR_b surfaces, with FN and PR_a being second and third, respectively (FIG. 2). FIGS. 1 and 2 collectively demonstrate that for all the peptide surfaces that include the PHSRN sequence (50% GRGDSP-50% PHSRN, PR_a, and PR_b), the PR_b is the only fibronectin-mimetic sequence that compares favorably with FN, and remaining studies were performed between FN, PR_b, GRGDSP and GRGESP surfaces.

Figure 3:
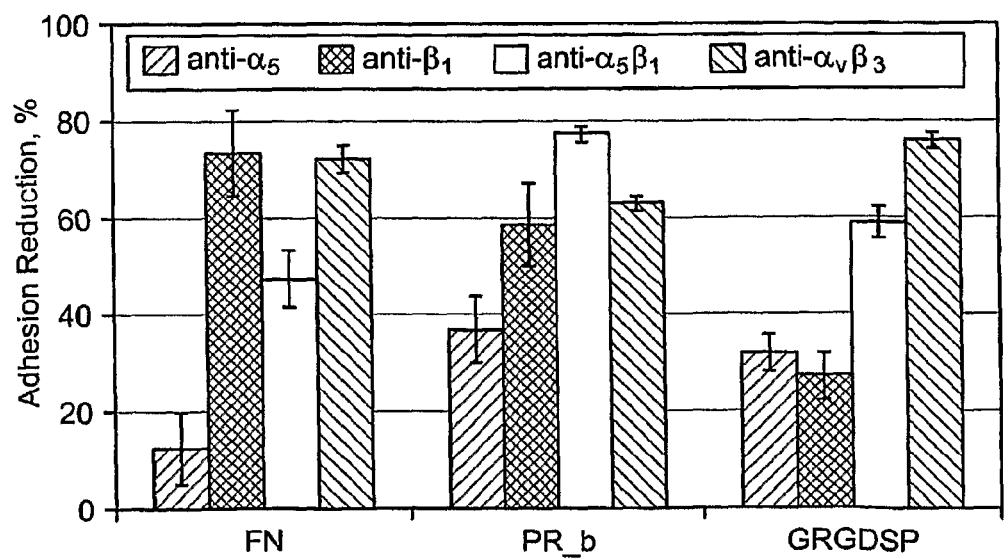
FIG. 3. Integrin specificity. Inhibition assay using anti-integrin blocking antibodies against as (P1D6), $\beta_1$, (P5D2), $\alpha_5\beta_1$ (JBS5), and $\alpha_v\beta_3$ (LM609) to determine integrin engagement profile for HUVEC adhesion on FN, PR_b, and GRGDSP substrates after 1 hr incubation at 37° C. and 5% $CO_2$, in the absence of fetal bovine serum. Results are reported as percentage of reduction in cell adhesion by blocking antibodies compared to the control (non blocked cells).

Integrin specificity was examined by blocking HUVECs with anti-$\alpha_5$, anti-$\beta_1$, anti-$\alpha_5\beta_1$, and anti-$\alpha_v\beta_3$ monoclonal antibodies, and then incubating blocked cells on PR_b, GRGDSP, and FN surfaces for 1 hour (FIG. 3). Cell adhesion on FN was equally reduced by anti-$\beta_1$ (73.84±8.69% reduction in cell adhesion compared to adhesion of non-blocked cells), and anti-$\alpha_v\beta_3$ (72.39±2.87%). HUVEC adhesion on GRGDSP was reduced the most by anti-$\alpha_v\beta_3$ (75.99±1.51%), whereas cell adhesion on PR_b surface was reduced the most by the anti-$\alpha_5\beta_1$ antibody (77.55±1.50%). This indicates that HUVEC adhesion to PR_b surfaces was $\alpha_5\beta_1$-mediated.

To investigate cytoskeletal organization and focal adhesion formation, HUVECs seeded on PR_b, GRGDSP, and GRGESP membranes and FN surfaces were fixed and stained at 1, 12, 24, 48, and 72 hours for actin stress fibers, nuclei, and vinculin, a major protein present in focal contacts (Jockusch et al., *Annu. Rev. Cell Dev. Biol.*, 1995; 11:379-416). At 12 hours of incubation on the inactive GRGESP surface, HUVECs began to collapse into a spindle-shaped morphology with no distinct actin fibers and very few focal adhesion points. Cells seeded on GRGDSP surfaces showed some actin fiber formation at 12 hours, though at 24 hours, actin organization became less pronounced. Cells did not form strong focal adhesion contacts on GRGDSP surfaces and vinculin was present mainly in the perinuclear area of the cells. HUVECs seeded on both FN and PR_b surfaces displayed actin stress fibers and focal contacts for 1-72 hours. However, cells on PR_b clearly showed a better-developed cytoskeletal structure compared to FN, suggesting a more firm adhesion on the fibronectin-mimetic peptide, PR_b, (which is in agreement with cell adhesion data in FIG. 1). Adherent cells to PR_b, for 1-72 hours, assembled longer, thinner vinculin-positive focal adhesion complexes compared to FN, with sharp spikes of vinculin at the termination points and across the actin stress fibers. Strong actin cytoskeleton organization into elongated stress fibers was also more pronounced at all times on PR_b compared to FN surfaces.

Extracellular fibronectin production was observed at 12 hours of incubation on all surfaces, and may explain the increase in cell adhesion from 4 to 12 hours observed in FIG. 1. Secreted fibronectin was labeled with an anti-human fibronectin monoclonal antibody, specific for secreted fibronectin, and thus was distinguished from the FN coated glass slides. Therefore, fluorescent labeling of secreted fibronectin was only observed in the vicinity of the adhered cells, and not in the areas without cells. Fibronectin production on GRGDSP and GRGESP surfaces was significantly less compared to FN and PR_b at 12 and 24 hours. After 48 hours of incubation, there was minimal fibronectin secretion that was not sufficient to sustain cell adhesion on GRGDSP and GRGESP surfaces. This result is also in agreement with data from FIG. 1, where cell density on these two substrates dramatically decreases after 48 hours. The amount of fibronectin secretion was found to increase with incubation time on the two adhesive surfaces (FN and PR_b), and was comparable for both substrates at all times examined. In addition, after 48 hour for both PR_b and FN, the areas around and under the cells were fully covered with secreted fibronectin. This finding is significant considering that extracellular protein production is of relevant for the viability and success of any functionalized biomaterial as a tissue engineering construct.

Conclusions

A new PR_b peptide-amphiphile was designed in this study that mimics fibronectin's cell binding domain, and is specific for $\alpha_5\beta_1$ integrins. Performance of PR_b was evaluated in terms of cell adhesion, spreading, cytoskeletal organization, and extracellular fibronectin production. Results were compared to our earlier design of the fibronectin-mimetic peptide-amphiphile, PR_a, as well as to a surface with equimolar amounts of GRGDSP and PHSRN, and to pure GRGDSP, GRGESP, and FN surfaces. PR_b outperformed all other peptide substrates, and compared favorably to FN. This is the first study demonstrating that a peptide gives stronger cell adhesion than FN for 1-24 hours. This result can be attributed first to the PR_b peptide sequence accurately mimicking the cell binding domain of fibronectin, and second, to a higher molar concentration of PR_b compared to FN, an advantage peptides have over protein functionalized interfaces (the ratio of PR_b:FN molecules was approximately 470:1). After 48 hours, cell adhesion was equivalent on both PR_b and FN due to high amounts of secreted ECM fibronectin that had covered areas under and around the cells. In addition, HUVECs were found to spread the most on the PR_b surfaces for all times examined, from 1 to 72 hours. Results from immunocytochemical studies showed that compared to FN, the PR_b sequence can effectively promote stronger cytoskeletal organization and focal adhesion formation.

In summary, the results presented here demonstrate the value of biomimetic surface science. The novel peptide sequence (PR_b) can find applications in biomaterial functionalization, tissue engineering, and targeted drug delivery.

Example 2

This example describes the design and systematic study of four peptide-amphiphiles to examine the effect of linker length, hydrophobicity/hydrophilicity, and the effect of spacer length on human umbilical vein endothelial cell adhesion and fibronectin production. The spacer and linker design of Pr_b was shown to give the most consistent adhesion over 12 hours, to give good fibronectin production at 12 hours, and to outperform the positive control fibronectin at all times. In addition to confirming the excellent performance of Pr_b, this work also outlines a logical approach that can be applied to the future design of any protein-mimetic peptide that combines two active binding sites.

Materials and Methods

Isotherm preparation: All six peptide-amphiphiles, as shown in Table 2, were synthesized as described elsewhere (Berndt, *J. Am. Chem. Soc.*, 1995; 117:9515-9522). To obtain a surface pressure-area isotherm for each peptide-amphiphile, the Langmuir Blodgett (LB) technique was used on a KSV 5000 LB system (KSV Instruments) as previously described (Mardilovich, *Langmuir*, 2005; 21:7468-7475), but with water obtained from a MilliQ Biocell system (Millipore) and then autoclaved before use.

TABLE 2

Peptide-Amphiphile Structures and Nomenclature.

| Peptide-amphiphile structure | Abbreviation | Spacer length (3.7 Å/amino acid[a]) | Linker length (3.7 Å/amino acid[a]) |
|---|---|---|---|
| $(C_{16})_2$-Glu-$C_2$-PHSRNSGSGSGSGSGRGDSP | Pr_a | — | 29.6 Å |
| $(C_{16})_2$-Glu-$C_2$-KSSPHSRNSGSGSGSGSGRGDSP | Pr_b | 11.1 Å | 37 Å |
| $(C_{16})_2$-Glu-$C_2$-KSSPHSRNGGGGGGGGGRGDSP | Pr_c | 11.1 Å | 37 Å |
| $(C_{16})_2$-Glu-$C_2$-KSSPHSRNSSSSSSSSSSRGDSP | Pr_d | 11.1 Å | 37 Å |
| $(C_{16})_2$-Glu-$C_2$-PHSRNSGSGSGSGSGRGDSP | Pr_e | — | 37 Å |
| $(C_{16})_2$-Glu-$C_2$-KSSSSSPHSRNSGSGSGSGSGRGDSP | Pr_f | 22.2 Å | 37 Å |

[a]Idiris et al., Protein Eng., 2000; 13: 763-770; Kokkoli et al., Langmuir, 2004; 20: 2397-2404

Surface preparation: Each peptide-amphiphile was used to form homogenous LB membranes as in previous work (Kokkoli Langmuir 2004; 20:2397-2404), except that both the water and 15 mm mica disks used had been autoclaved for sterility. All depositions were done at a surface pressure between 41 and 47 mN/m, well below the collapse pressure and in the liquid-condensed or solid phase. Approximately 90 minutes before cells were seeded on the LB films to begin cell adhesion experiments, mica surfaces were transferred into 1× phosphate buffered saline (PBS), with particular care taken to ensure films were not exposed to air. After 5-10 minutes of equilibration, surfaces were transferred into 24-well plates containing a supplemented MCDB-131 basal media (Sigma), as described in Example 1. Following surface transfer, 24-well plates were moved to a 37° C., 5% $CO_2$ incubator for 45-60 minutes. As a control, 22 mm diameter human fibronectin-coated coverslips (BD Biosciences), referred to as FN, were put into 12-well plates, covered with 2 ml of the supplemented media, and also incubated for 45-60 minutes.

Cell culture: Human umbilical vein endothelial cells, HUVECs (Cambrex Corporation), were cultured as described previously (see Example 1). Only cells from passage 3 were used in all studies.

Cell adhesion experiments: Flasks of HUVECs with at least 90% confluency were washed with 1×PBS, trypsinized with 0.25% Trypsin-EDTA (Fisher Scientific), and neutralized with 2% fetal bovine serum in MCDB-131 basal media. The suspended cells from all flasks were placed in one 50 ml centrifuge tube and centrifuged at 1000 rpm for 5 minutes. The media was removed and the cell pellet was resuspended in the supplemented media described above. A hemocytometer was used to count the cells and then 497 cells/mm$^2$ were seeded onto both LB and FN surfaces. Surfaces were incubated with cells at 37° C., 5% $CO_2$ for 1, 4, or 12 hours. Cell adhesion following these times was determined using the CyQuant cell proliferation assay kit (Molecular Probes), which measures the fluorescence of a cellular nucleic acid-binding dye using the SpectraMAX GeminiXS plate reader (Molecular Devices). Standard calibration curves were created within each experiment for both 12- and 24-well plates.

Fibronectin production staining: Surface preparation, transfer, and cellular work were all done as described in the previous methods. Only surfaces incubated with cells for 12 hours were stained. The staining protocol, involving a primary antibody for secreted fibronectin (Chemicon), a FITC-conjugated secondary antibody (Chemicon), and the Image-iT LIVE plasma membrane and nuclear labeling kit (Molecular Probes), was done as previously described in Example 1. A single photon confocal microscope (Olympus FluoView FV1000) was used for imaging. Two slides per substrate were prepared each during 2 separate experiments and each slide was imaged 2-4 times. The final images chosen were all taken from one experiment for consistency, but were representative of the images obtained from both experiments.

Results

Figure 4:
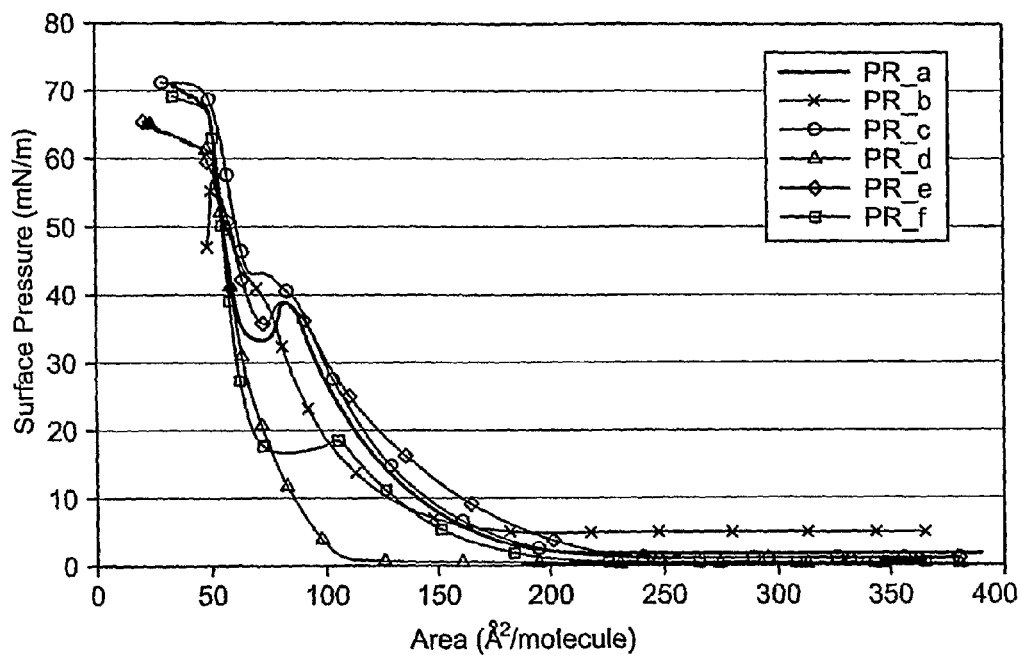
FIG. 4. Surface pressure-area compression isotherms of amphiphilic molecule in a sterilized water subphase at room temperature.

Surface pressure-area compression isotherms obtained from the six peptide-amphiphiles studied are shown in FIG. 4. All peptide-amphiphiles show a phase transition at a pressure somewhere between 18 and 45 mN/m except for Pr_d. Also, all six peptide-amphiphiles show a collapse pressure above the deposited pressures of 41 to 47 mN/m. This collapse pressure ranges from 57 to 71 mN/m.

Figure 6:
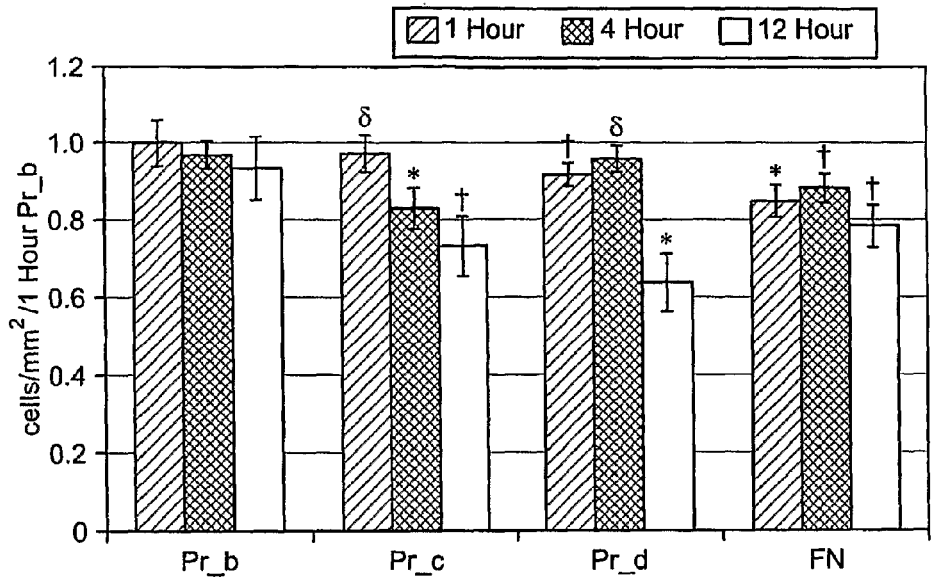
FIG. 6. Effect of linker hydrophobicity/hydrophilicity on HUVEC adhesion to novel peptide. Cell adhesion was evaluated on LB membranes of Pr_b, Pr_c, and Pr_d and the positive control FN at 1, 4, and 12 hours. HUVECs were incubated at seeding density 497 cells/mm$^2$ on substrates at 37° C., 5% CO) in the absence of serum. Results are given as the cell density value for each particular surface and time period divided by the cell density value of Pr_b at 1 hour. Symbols above a particular column represent the p-value given the null hypothesis that that column's adhesion density and the Pr_b adhesion density for that same time period (i.e. 1, 4, or 12 hours) are the same. z-test analysis for δ: p<0.7, indicating no statistical difference; z-test analysis for †: p<0.03, indicating a statistically significant difference; z-test analysis for ✽: p<0.001, indicating very strong evidence of a statistically significant difference. Each histogram represents the mean±SD. For all substrates, n=3 (three independent experiments performed on different days).
Figure 7:
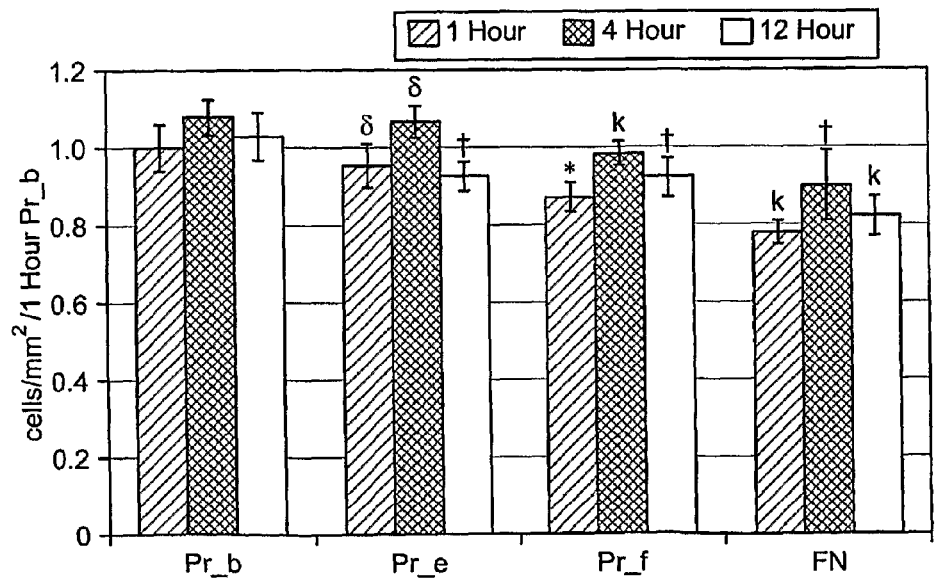
FIG. 7. Effect of spacer length on HUVEC adhesion to novel peptides. Cell adhesion was evaluated on LB membranes of Pr_b, Pr_e, and Pr_f and the positive control FN at 1, 4, and 12 hours. HUVECs were incubated at seeding density 497 cells/mm² on substrates at 37° C., 5% $CO_2$ in the absence of serum. Results are given as the cell density value for each particular surface and time period divided by the cell density value of Pr_b at 1 hour. Symbols above a particular column represent the p-value given the null hypothesis that that column's adhesion density and the Pr_b adhesion density for that same time period (i.e. 1, 4, or 12 hours) are the same. z-test analysis for δ: p<0.7, indicating no statistical difference; z-test analysis for †: p<0.03, indicating a statistically significant difference; z-test analysis for ✷: p<0.001, indicating very strong evidence of a statistically significant difference. Each histogram represents the mean±SD. For all substrates, n=3 (three independent experiments performed on different days).

FIGS. 5-7 display the results of the cellular adhesion timed experiments. FIG. 5 compares adhesion when no spacer is present in the peptide-amphiphile. Thus, the only difference between the two peptide-amphiphiles compared is the length of the linker, with Pr_a containing only four serine-glycine pairs versus Pr_e's five pairs. This gives Pr_e an approximately 7.4 Å longer linker between the PHSRN and RGDSP amino acid sequences. In FIG. 6, the importance of the hydrophobicity/hydrophilicity of the linker between the PHSRN and the RGDSP sequences is tested. All three peptide-amphiphiles contain the same spacer, as well as the same number of amino acids, and thus length, in the linker. Pr_b's linker is composed of five hydrophilic serines alternating with five hydrophobic glycines and is neutral overall, whereas Pr_c's linker is 10 hydrophobic glycines and Pr_d's linker is 10 hydrophilic serines. Finally, in FIG. 7, the comparison is in the length of the spacer, with all three peptide-amphiphiles containing the exact same linker sequence (—(SG)$_5$-). Pr_e contains no spacer at all, Pr_b contains the three amino acid sequence of a lysine followed by two serines, and Pr_f's spacer adds another three serines, increasing its length by 11.1 Å as compared to PR_b. In all three figures, cellular adhesions to FN are also given for comparison.

Discussion

The surface pressure-area compression isotherms shown in FIG. 4 were done in order to determine if and at what surface pressure each peptide-amphiphile shows a phase transition, as well as each one's ultimate collapse pressure. The four peptide-amphiphiles Pr_a, Pr_b, Pr_c, and Pr_e all show similar behavior, with secondary phase transitions in the peptide-headgroup, indicated by the hump in the isotherm (Dillow, *Biomaterials*, 2001; 22:1493-1505), occurring at pressures between 35 and 45 mN/m. Pr_f also shows a similar phase transition, although at the much lower surface pressure of 18.5 mN/m. This is attributed to the longer length of the Pr_f peptide headgroup. Pr_f's headgroup is the longest of all the peptide-amphiphiles with 26 amino acids. This longer headgroup, containing three extra hydrophilic serines in the N-terminus-oriented spacer, takes up more room and spreads itself out more on the surface of the water as compared to the other peptides. As the barriers compress and the surface area decreases, Pr_f's headgroups begin to feel each other's presence at lower surface pressures and are forced to transition from a bent to extended configuration earlier. The final peptide-amphiphile, Pr_d, behaves much differently from those previously discussed because no secondary phase transition is present in its isotherm. This peptide headgroup contains 10 serine residues as the linker between the PHSRN and RGD active sequences. Each of these serines contain a carboxylic acid, which is available to form hydrogen bonds with other serines, both within its own molecule and between neighboring Pr_d molecules. A network of hydrogen-bonded headgroups then forms that does not undergo any straightening phase transition until the monolayer collapses at 60 mN/m. This hydrogen-bonding network also resulted in low transfer ratios, between 0.4-0.6, when the Pr_d was deposited onto the mica surfaces. All other peptide-amphiphiles had transfer ratios between 0.8-1, indicating little disturbance in the transferred monolayer. Finally, all peptide-amphiphile monolayers collapse into three dimensional structures between 57 and 71 mN/m. All depositions onto mica are done at surface pressures between 41 and 47 mN/m, always after the secondary phase transition, when the monolayer is in the solid-condensed phase, but well before the ultimate collapse.

The timed experiment adhesion results in FIG. 5 examine the effect of different linker length between the PHSRN and RGDSP sequences, with Pr_e's linker containing an extra serine-glycine pair. At the 1 hour time period, Pr_e gives higher HUVEC adhesion than both Pr_a ($p<0.03$) and FN ($p<0.001$), with Pr_a and FN's adhesion showing no statistical difference ($p<0.7$). At the 4 hour time period, there is no statistical difference in the level of adhesion between Pr_e and Pr_a, although comparison of the averages alone shows that Pr_e is slightly higher. Pr_e also shows higher adhesion than FN ($p<0.03$). Pr_a and FN show no difference in adhesion at 4 hours. Finally, for the longest time, 12 hours, Pr_e and Pr_a are again not statistically different, although Pr_e's average is slightly higher. Pr_e is statistically higher than FN ($p<0.001$), as is Pr_a, though at the lower significance level of $p<0.03$. Overall, it is evident that Pr_e gives superior cell adhesion performance as compared to Pr_a, as well as the control FN, and thus it can be concluded that the longer, ten amino acid linker stretching 37 Å, is the best choice.

Given that the longer linker is desirable as shown in FIG. 5, the next question to examine is the hydrophobicity/hydrophilicity of the linker. This comparison is done using three peptide-amphiphiles designed to have the same spacer (KSS) and the same number of amino acids in the linker. All three linkers use only serines and/or glycines, with Pr_b's linker being neutral overall, Pr_c's hydrophobic, and Pr_d's hydrophilic. FIG. 6 shows that Pr_b performs significantly better than Pr_c at all times except 1 hour, better than Pr_d at all times except 4 hours, and better than FN at all times. Even in the two cases that Pr_b is not significantly better, Pr_b's adhesion is at least slightly higher than the other two. Pr_c's high adhesion at 1 hour can be attributed to hydrophobic interactions between the polyglycine linker and hydrophobic cell membranes, which explains why this level of adhesion is not maintained at longer time periods. Also, adhesion to RGD-PHSRN peptides with polyglycine linkers, like Pr_c, has been shown to be mediated by the $\alpha_v\beta_3$ integrin (Petrie, *Biomaterials*, 2006; 27:5459-5470). Thus, Pr_c is not specific to the $\alpha_5\beta_1$ integrin. Prod shows good adhesion out to 4 hours, but the extreme drop-off at 12 hours makes this a poor choice for long-term adhesion. Overcall, Pr_b shows excellent adhesion at all times, always significantly higher than the control FN, as well as giving the smallest amount of decay over 12 hours.

Another factor to consider when designing a fibronectin-mimetic peptide is the length of the spacer that extends the active sites away from the surface of the membrane. FIG. 7 shows the adhesion results for Pr_b, containing a three amino acid spacer KSS, as compared to Pr_e with no spacer and Pr_f with a six amino acid spacer KSSSSS. For all time periods, Pr_b performs statistically better than both Pr_f and the control FN. When comparing Pr_b and Pr_e, there is no statistical difference between the averages for 1 and 4 hours, although in both cases, Pr_b's average is slightly higher. At 12 hours, Pr_b outperforms Pr_e at a significance level of $p<0.03$. Also, Pr_b's adhesion level shows the least drop-off between 4 and 12 hours. This is particularly significant because past work has shown that adhesion is maintained between 12 and 24 hours due to the start of fibronectin production by the cells (Example 1). Thus, the higher 12 hour adhesion equates to higher long-term adhesion as well. Overall, Pr_b's three amino acid spacer seems to allow the best adhesion, extending the active sequences the optimal distance off the surface of the bilayer membrane to better expose them to the $\alpha_5\beta_1$ integrins.

Extracellular matrix protein production by cells adhered to a surface indicates that the cells are content and allows them to maintain adhesion long-term. Once cells form their own matrix, the original surface, in this case the bilayer peptide-amphiphile membrane, is no longer seen by cell integrins and becomes irrelevant to their continued adhesion. One of these excreted ECM proteins is fibronectin. Fibronectin begins to be produced by adhered cells sometime between the 4 and 12 hour time periods, so fibronectin staining was done only on 12 hour surfaces. Fibronectin was labeled using an anti-human fibronectin monoclonal antibody specific to secreted fibronectin. The goal of the fibronectin staining was to ensure that adhered cells on all surfaces were producing ECM, thus supporting each surface's respective level of adhesion. All surfaces, including both the six peptide-amphiphile surfaces and the control FN, allow both cell adhesion and ECM production as seen from the presence of secreted fibronectin on all. This finding demonstrates that all six versions of the fibronectin-mimetic peptide engineered here present the primary and secondary active binding sites, RGD and PHSRN respectively, to HUVEC $\alpha_5\beta_1$ integrins, allowing some level of cell adhesion. The fibronectin's presence at 12 hours also agrees with the experimental parameter of ending the timed experiments at 12 hours because by that time, produced ECM surrounds the cells and blocks interaction with any remaining peptide.

Conclusion

Six peptide-amphiphile designs containing the primary binding sequence RGD and the $\alpha_5\beta_1$ integrin-specific synergy site PHSRN were tested for their ability to induce cell adhesion and ECM production in human umbilical vein endothelial cells. The peptide-amphiphiles were systematically constructed in order to test the effect of length and hydrophobicity/hydrophilicity in the linker connecting the PHSRN to the RGD sequence, as well as the effect of the length of the spacer used between the amphiphile's hydrophobic tails and the headgroup's active sites. When linker length was compared, Pr_e, with a 10 amino acid linker, outperformed both Pr_a's 8 amino acid linker and the control FN. The longer 10 amino acid linker was then used in the remainder of the adhesion experiments. Linker hydrophobicity/hydrophilicity was compared using Pr_b, Pr_c, and Pr_d. Pr_b's neutral linker allowed the highest level of adhesion with the least amount of decay over the 12 hour time period. Finally, when the effect of spacer length was compared, Pr_b's three amino acid spacer performs much better than Pr_f's 6 amino acid spacer at all times and better than Pr_e with no spacer at the important 12 hour time. It was seen from secreted fibronectin staining that all six peptide-amphiphile surfaces, as well as the positive control FN, allowed attached cells to produce fibronectin. This indicates that all six designs are capable of successfully mimicking fibronectin's cell binding domain to some degree. Based on the adhesion experiments, however, the current best choice for use in biomaterial or drug delivery applications is Pr_b.

The strategy employed in this work for designing a fibronectin-mimetic peptide can be used for future work anytime two active sites are being combined in one peptide to mimic a protein. Using a spacer to expose the active sites and a linker to mimic the protein's natural distance between the active sites provides an initial design. The methodical approach employed in this work for determining the spacer and linker lengths and linker hydrophobicity/hydrophilicity can then be used to focus in on one best possible design.

Example 3

This example describes the design of functionalized stealth liposomes (liposomes covered with polyethylene glycol (PEG)) that will specifically target the integrin $\alpha_5\beta_1$. The PEG provides a steric barrier allowing the liposomes to circulate in the blood and the functionalizing moiety, PR_b peptide, will specifically recognize and bind to $\alpha_5\beta_1$, expressing cells. This example demonstrates that by optimizing the amount of PEG and PR_b on the liposomal interface it is possible to engineer nano-vectors that bind to CT26.WT, HCT116, and RKO colon cancer cells in a specific manner and are internalized through $\alpha_5\beta_1$-mediated endocytosis. GRGDSP-targeted stealth liposomes bind to colon cancer cells and internalize, but they have much lesser efficiency than PR_b targeted stealth liposomes. The proposed targeted delivery system has a great potential to deliver chemotherapeutic agents directly to colon cancer cells, in an efficient and specific manner.

Methods

Figure 8:
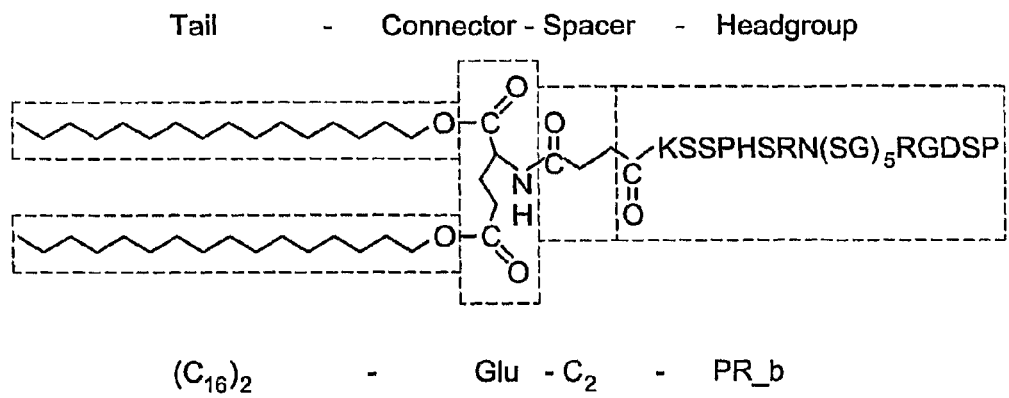
FIG. 8. Structure of PR_b peptide-amphiphile.

Materials: Lipids, 1,2-Dipalmitoyl-sn-Glycero-3-Phosphocholine (DPPC), cholesterol (CHOL), 1,2-Dipalmitoyl-sn-Glycero-3-Phosphoethanolamine-N-(Methoxy(Polyethylene glycol)-750)-Ammonium Salt) (PEG750) and 1,2-Dipalmitoyl-sn-Glycero-3 Phosphoethanolamine-N-(Methoxy(Polyethylene glycol)-2000)-(Ammonium Salt) (PEG-2000) were purchased from Avanti Polar Lipids Inc. (Alabaster, Ala.). The extruder and the 100 nm polycarbonate membranes were obtained from Avestin Inc. (Ottawa, Canada). The peptide headgroups PR_b (KSSPHSRN(SG)$_5$RGDSP) and GRGDSP (KAbuGRGDSPAbuK, where Abu is 2-aminobutyric acid) were purchased in crude form from the Microchemical Facility at the University of Minnesota. The peptide-amphiphiles, PR_b peptide-amphiphile (($C_{16}$)$_2$-Glu-$C_2$-KSSPHSRN(SG)$_5$RGDSP) (FIG. 8) and GRGDSP peptide-amphiphile (($C_{16}$)$_2$-Glu-$C_2$-KAbuGRGDSPAbuK) were synthesized as described previously (see Example 1) (Mardilovich, *Biomacromolecules*, 2004; 5, 950-957; and Berndt, *Journal of the American Chemical Society*, 1995; 117:9515-9522). CT26.WT (mouse colon cancer cell line) were a gift from Prof. McIvor and human colon cancer cell lines HCT116 and RKO were obtained from ATCC (Manassas, Va.). Hoechst 33342 nucleic stain, Alexa Fluor® 594 wheat germ aggutin (WGA) cell membrane stain, and ProLong Gold antifade reagent were purchased from Invitrogen Corporation (Carlsbad, Calif.). Primary polyclonal antibody anti-integrin $\alpha_5\beta_1$ and secondary antibody donkey anti-Goat IgG FITC conjugated were purchased from Chemicon International Inc. (Temecula, Calif.). Goat IgG isotype control was purchased from Sigma Aldrich Corporation (St. Louis, Mo.). Cell culture media was purchased from ATCC (Manassas, Va.), fetal bovine serum (FBS) was purchased from Atlas Biologicals (Fort Collins, Colo.), and human fibronectin-coated round coverslips were purchased from BD Biosciences (San Jose, Calif.). All other reagents were purchased from Sigma Aldrich Corporation (St. Louis, Mo.) and were of biotechnology performance certified grade.

Cell Culture: CT26.WT cell lines were grown in RGM (modified RPMI-1640 medium supplemented with 10% FBS, 2 mM L-Glutamine, 100 units/ml Penicillin, and 0.1 mg/ml Streptomycin). Cells were grown in T-75 flasks with a feeding cycle of 2 days. After cells became 80% confluent (usually after 5 days) they were trypsinized (0.25% Trypsin+ 0.1% EDTA) and were suspended in RGM. Cells were washed twice and finally were frozen under liquid nitrogen in RGM containing 10% DMSO (dimethyl sulfoxide) for future use. For subsequent passages cells were seeded in fresh T-75 flasks at a density 10,000 cells/cm$^2$ and were cultured in RGM with a feeding cycle of 2 days. HCT116 cell lines were grown in MGM (modified McCoy's 5A medium, supplemented with 10% FBS, 2 mM L-Glutamine, 100 units/ml Penicillin, and 0.1 mg/ml Streptomycin) and RKO cells were grown in EGM (modified Eagle's Minimum essential medium, supplemented with 10% FBS, 2 mM L-Glutamine, 100 units/ml Penicillin, and 0.1 mg/ml Streptomycin)

Liposome preparation and characterization: Liposomes were prepared as described elsewhere (Fenske, 2003, Encapsulation of weakly-basic drugs, antisense oligonucleotides, and plasmid DNA within large unilamellar vesicles for drug delivery applications, in *Liposomes*, 2 ed., Oxford University Press, New York). Briefly, lipids were dissolved in chlorofoun and peptide-amphiphiles were dissolved in methanol and water. Lipids and peptide-amphiphile were combined at the ratios (65-x-y):35:x:y mol % of DPPC:CHOL:PEG:Peptide-Amphiphile, where x is the indicated molar ratio of PEG750 or PEG2000 and y is the molar ratio of peptide-amphiphile. Solvents were removed by evaporating under a gentle stream of argon at 65° C. and lipids were dissolved again in chloroform to form a homogenous mixture. The lipid mixture was finally dried under a gentle stream of argon at 65° C. until a uniform lipid film was formed, followed by drying under vacuum overnight. The lipid film was hydrated with fluorescent HBSE buffer (10 mM Hepes, 150 mM NaCl, 0.1 mM EDTA, and 2 mM Calcein) at 65° C. at a concentration of 10 mM total lipids. Hydrated lipids were freeze-thawed five times, then extruded for 21 cycles through two stacks of 100 nm polycarbonate membranes using the hand-held extruder (Avestin Inc., Ottawa, Canada). Liposomes were filtered over a Sepharose CL-4B gel filtration column to remove unencapsulated fluorescent dye and other molecule, which are not incorporated in the liposomes. Liposome diameter was determined by dynamic light scattering and ranged from 80-150 nm. Phospholipid concentration was determined using the phosphorus colorimetric assay described elsewhere (Chen, *Analytical Chemistry*, 1956; 28:1756-1758; Fiske, *Journal of Biological Chemistry*, 1925; 66, 375-400). Liposomes were stored at 4-8° C. and were used within two weeks. Peptide concentration was determined using BCA assay according to the manufacturer's protocol. We were not able to accurately determine the PEG concentration due to experimental limitations (see Example 4); therefore, in the text we address PEG concentration either as low when 2 mol % PEG was included in starting lipid concentration or as high when 5 mol % PEG was used in the starting lipid concentration.

Flow cytometry: CT26.WT confluent cell monolayers were trypsinized (0.25% Trypsin+0.1% EDTA) and resuspended in ice-cold FB (fluorescent buffer: phosphate buffered saline (PBS) supplemented with 0.02% sodium azide and 2.5% fetal bovine serum) containing liposomes at a lipid concentration of 250 µM and a cell concentration of 1 million/ ml in 15 ml centrifuge tubes. Tubes were incubated at 4° C. or 37° C. over a rotary shaker for the specified duration of time. Cells were then pelleted and washed twice in FB. Flow cytometric analysis was carried out immediately. For peptide blocking experiments, the protocol specified above was used except cells were incubated with 200 µg/ml of free peptide-amphiphile in FB for one hour prior to incubating the cells with the liposomes. For integrin $\alpha_5\beta_1$ expression studies, CT26.WT confluent cell monolayers were trypsinized (0.25% Trypsin+0.1% EDTA) and resuspended in ice-cold FB at a cell concentration of 1 million/ml in 15 ml centrifuge tubes. Tubes were incubated at 4° C. with primary antibody (anti-integrin $\alpha_5\beta_1$) or goat isotype control (goat IgG) over a rotary shaker for 35 min. Cells were then pelleted and washed twice in FB and then incubated again with the secondary antibody (anti-goat IgG FITC conjugated) for 35 min. Finally, cells were pelleted and washed twice. Flow cytometric analysis was carried out immediately. FACS Calibur located at the Flow Cytometry Core facility in the Cancer Research Center of the University of Minnesota was used. All experiments were repeated twice but results are presented from a single experiment.

Confocal microscopy: CT26.WT confluent cell monolayers grown on fibronectin coverslips were incubated with liposomes at a lipid concentration of 250 µM, in a 5% $CO_2$ incubator at 37° C. or 4° C. for the specified duration in RGM. Cell monolayers were then washed with ice-cold FB twice. Cells were later fixed with a fixation buffer (4% paraformaldehyde in PBS, pH 7.4) for 15 min at 37° C. Nuclear staining was carried out using a cell membrane permeable blue-fluorescent Hoechst 33342 dye at a concentration of 2.0 µmole/ ml, and the cell membrane was stained with a cell impermeable red-fluorescent Alexa Fluor® 594 wheat germ aggutin (WGA) at 5.0 µg/ml in FB for 10 min. Cells were washed three times with FB, and coverslips were mounted on glass slides over ProLong Gold antifade reagent. For every sample 40 z-scans (horizontal cross-section of a cell at a particular z height) were taken at 0.25 µm z-step height to cover the entire height of the cell. On the confocal images liposomes were labeled with green, cell membrane with red and nucleus with a blue. Olympus Fluoview 1000 Confocal Laser Scanning Microscope at the Biomedical Image Processing Laboratory in the Department of Neuroscience at the University of Minnesota was used.

Results and Discussion

Figure 9A:
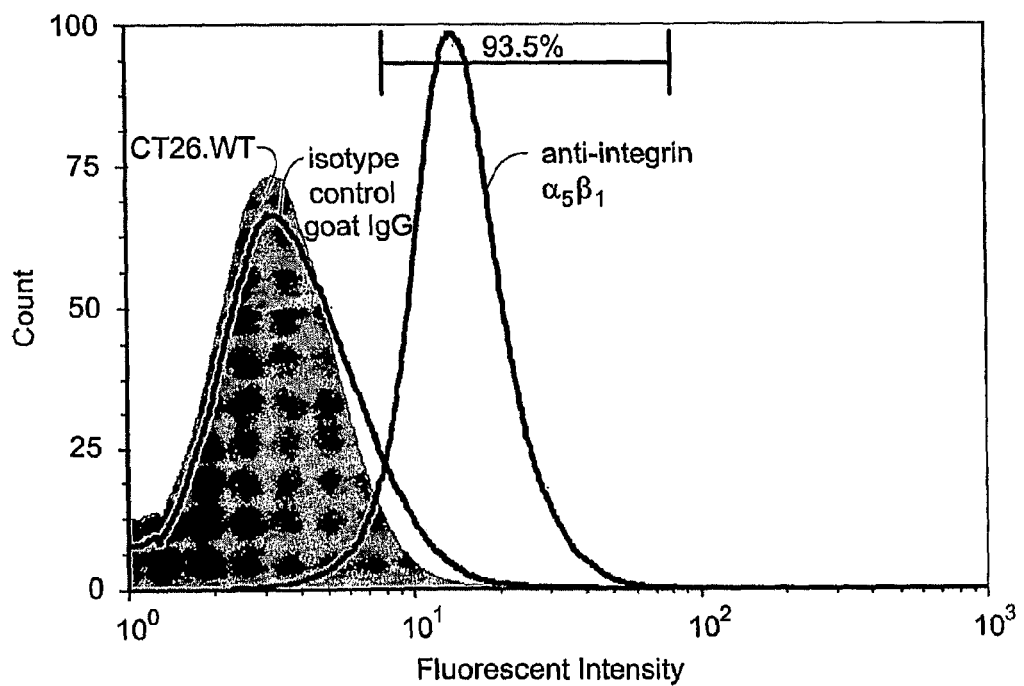
FIG. 9. Expression of integrin $\alpha_5\beta_1$ on a) CT26.WT b) HCT116 and c) RKO. Cells were incubated with antibodies to integrin $\alpha_5\beta_1$. Appropriate isotype control is included. The number on the marker represents the percentage of cells tested positive for integrin $\alpha_5\beta_1$ expression. The results are representative for n=2 but are shown only from one single experiment.
Figure 9B:
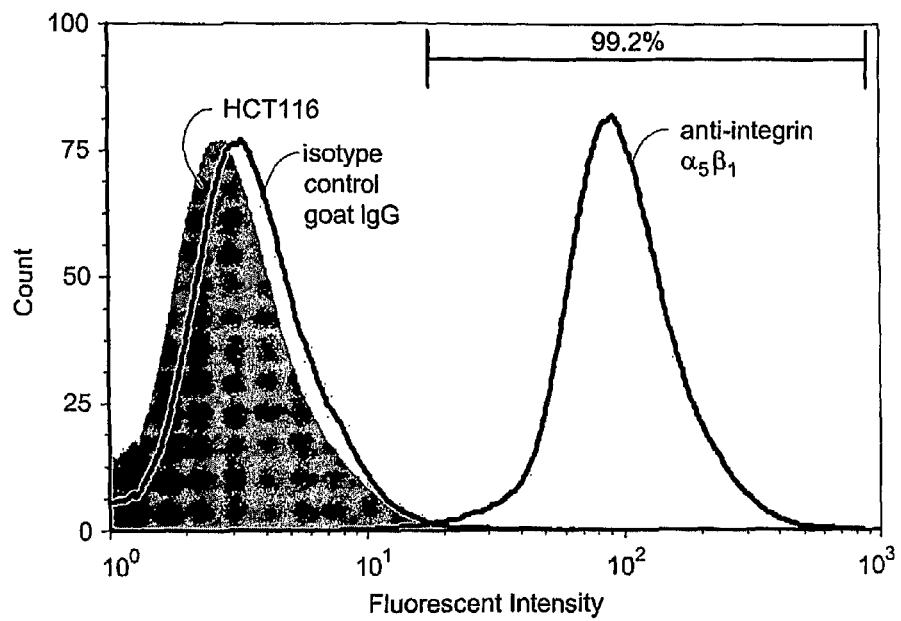
Figure 9C:
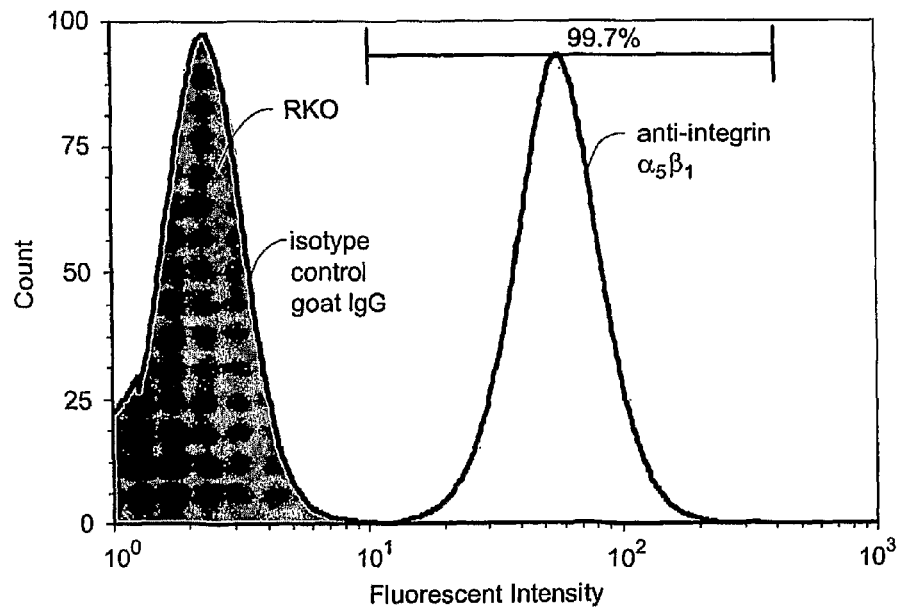

Expression of integrin $\alpha_5\beta_1$ on colon cancer cells. For a targeted drug delivery system to be effective the target should be significantly upregulated on the cells of interest. FIG. 9a shows the histogram for expression of $\alpha_5\beta_1$ on CT26.WT cells. 93.5% of the cell population tested positive for integrin $\alpha_5\beta_1$ expression. Isotype control binding was also characterized and was found to be minimal (shown oil the same histogram). This result confirms that integrin $\alpha_5\beta_1$ is highly upregulated on mouse colon carcinoma cells. Integrin $\alpha_5\beta_1$ expression was also found to be highly upregulated on human colon cancer cells HCT116 (FIG. 9b) and RKO (FIG. 9c).

Figure 10:
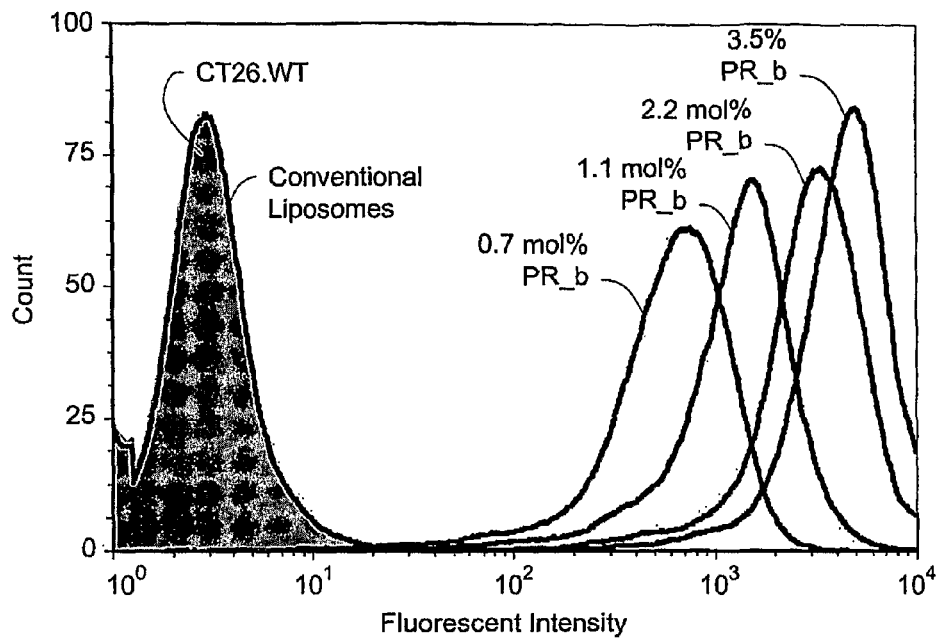
FIG. 10. Effect of concentration of PR_b peptide-amphiphile on binding of liposomes to CT26.WT cells at 4° C. for 3 hrs. Binding efficiency improves with increasing peptide concentration. Conventional liposomes show no binding to cells. The results are representative for n=2 but are shown only from one single experiment.

Effect of PR_b on liposome targeting. To test the effect of PR_b on the binding of liposomes to colon cancer cells, liposome formulations were initially prepared without PEG and with increasing amounts of PR_b peptide-amphiphile. Liposomes were incubated with cells for 3 hrs at 4° C. and 37° C. Cellular uptake of liposomes via endocytosis is inhibited at 4° C. because the endocytic pathways do not operate at lower temperatures (Lee, *Biochemistry*, 1993; 32:889-899; Kessner, *Biochimica et Biophysica Acta*, 2001; 1514:177-190). Therefore, conducting experiments at 4° C. allows studying the effect of peptide concentration oil surface binding of liposomes to cells with no interference from endocytosis. FIG. 10 shows the effect of peptide concentration on liposome binding to integrin $\alpha_5\beta_1$ expressing CT26.WT cells at 4° C. Similar trends were observed at 37° C. Conventional liposomes (liposomes containing DPPC/Chol and no PR_b peptide-amphiphile) show no binding to cells since their fluorescent intensity overlaps with the auto-fluorescence of the CT26.WT cells. Even a small concentration of PR_b, 0.7 mol %, gives sufficient binding to the colon cancer cells. Increasing the peptide concentration improves further the binding of the liposomes to the cells with maximum binding observed at the highest concentration of peptide studied, 2.2 and 3.5 mol %.

Effect of PR_b on stealth liposome targeting. Both the PEG layer thickness and the peptide concentration are relevant in designing a liposome delivery system. Longer PEG molecules (e.g. PEG2000) provide a better steric barrier but may mask the peptide molecule and hinder binding. Shorter PEG molecules (e.g. PEG750) may provide sufficient access for the peptide molecule to bind to the target receptor but may reduce the steric barrier. Therefore, two different lengths of PEG were studied, PEG750 and PEG2000. The goal of this study was to determine the optimal amount of both the peptide and PEG concentration on the liposome formulation. PEG was studied at two different concentrations, low (2 mol % starting concentration) and high (5 mol % starting concentration) and PR_b was included at a concentration of 2.2-2.6 mol % (the concentration at which maximum binding was observed in FIG. 10) and 1.1-1.2 mol %. The total concentration of PEG and PR_b did not exceeded above 8 mol %, as our work showed that when higher molecular weight molecules like PEG and peptide-amphiphiles were incorporated at a concentration of 8-10 mol %, that resulted in the destabilization of the liposome membrane. This was identified by the fact that when liposomes were filtered over a gel filtration column, chromatography results showed an additional peak between the absorbance peak for the liposomes and the absorbance peak for the free dye molecules. This suggested that these molecules form smaller structures other than liposomes.

Figure 11A:
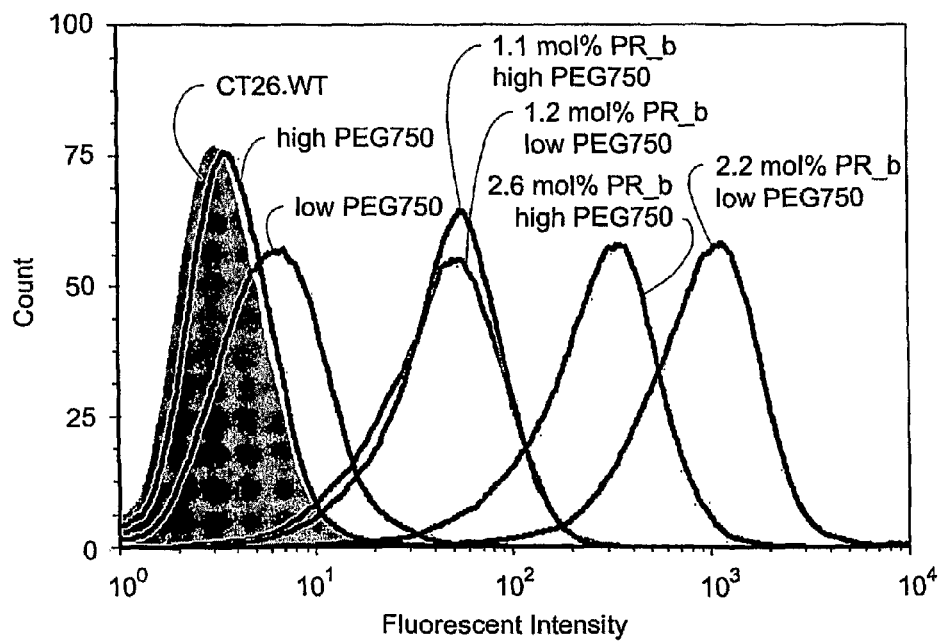
FIG. 11. Binding of PR_b-targeted stealth liposomes to CT26.WT cells at 4° C. for 3 hrs. The effect of PR_b concentration and PEG concentration and length were investigated. Low (2 mol % in the initial lipid mixture) and high (5 mmol % in the initial lipid mixture) concentrations of (a) PEG750 and (b) PEG2000 were considered. Significant binding affinities were achieved for liposomes functionalized with PR_b and PEG molecules compared to pegylated liposomes with no peptide. For both high and low concentrations of PEG750 and PEG2000, a concentration of 2-2.6 mol % PR_b peptide-amphiphile gave highest binding affinity to the CT26.WT cells. The results are representative for n=2 but are shown only from one single experiment.
Figure 11B:
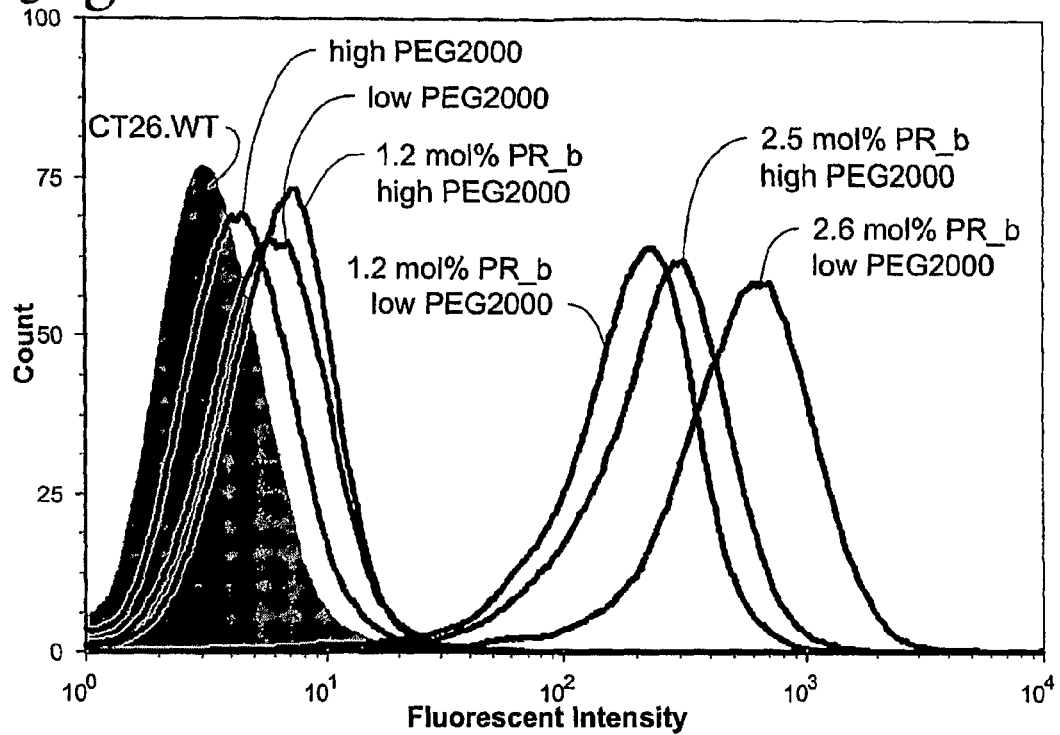

Flow cytometry results for PR_b functionalized pegylated liposomes targeted to CT26.WT for 3 hrs at 4° C. are shown in FIG. 11. Similar trends were observed at 37° C. Liposome binding to CT26.WT increased with increasing PR_b concentration and decreasing concentration for PEG750 (FIG. 11a) and PEG2000 (FIG. 11b). Conventional stealth liposome formulations (with no peptide-amphiphile) showed minimal binding. From the concentrations that were investigated, the maximum binding efficiency was achieved for a system containing 2.2-2.6 mol % peptide and low PEG concentration for both PEG750 and PEG2000. Liposome formulations with peptide concentrations of about 2.5 mol % and high PEG density were the next best option in terms of binding. Stealth liposomes with smaller peptide concentrations about 1.2 mol % showed reduced binding by at least one order of magnitude with the exception of 1.2 mol % PR_b and low PEG2000. A high PEG2000 concentration on a liposome system with a 1.2 mol % peptide concentration reduced the binding to a level similar to that observed for non-targeted stealth liposomes.

These results demonstrate the limitation of non-targeted stealth liposome systems currently being used in clinical practice. Although stealth liposomes can accumulate in tumor regions through passive targeting, they will not bind to tumor cells. Functionalizing these liposomes with peptides such as PR_b, designed to specifically target the integrin $\alpha_5\beta_1$ can help achieve higher binding efficiencies.

Figure 12A:
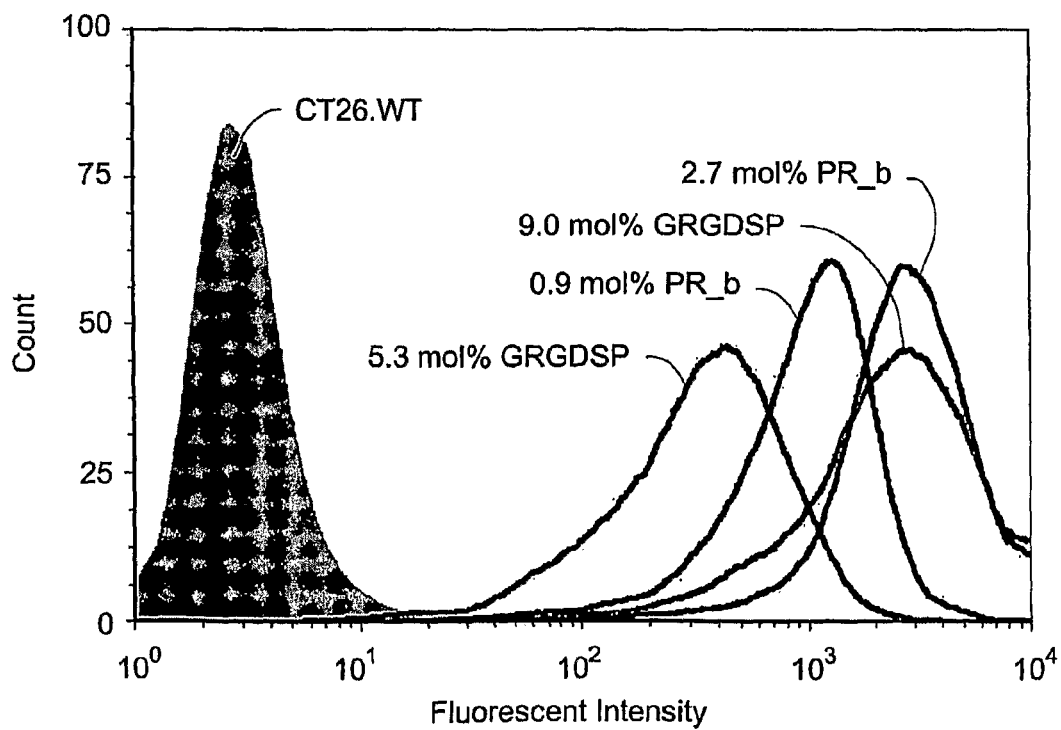
FIG. 12. Comparison of binding affinities between PR_b-targeted liposomes and GRGDSP-targeted liposomes with a) no PEG; b) PEG750; c) PEG2000. CT26.WT colon cancer cells were incubated with different liposome formulations for 3 hrs at 4° C. The results demonstrate that PR_b targeting is superior to GRGDSP targeting. The results are representative for n=2 but are shown only from one single experiment.
Figure 12B:
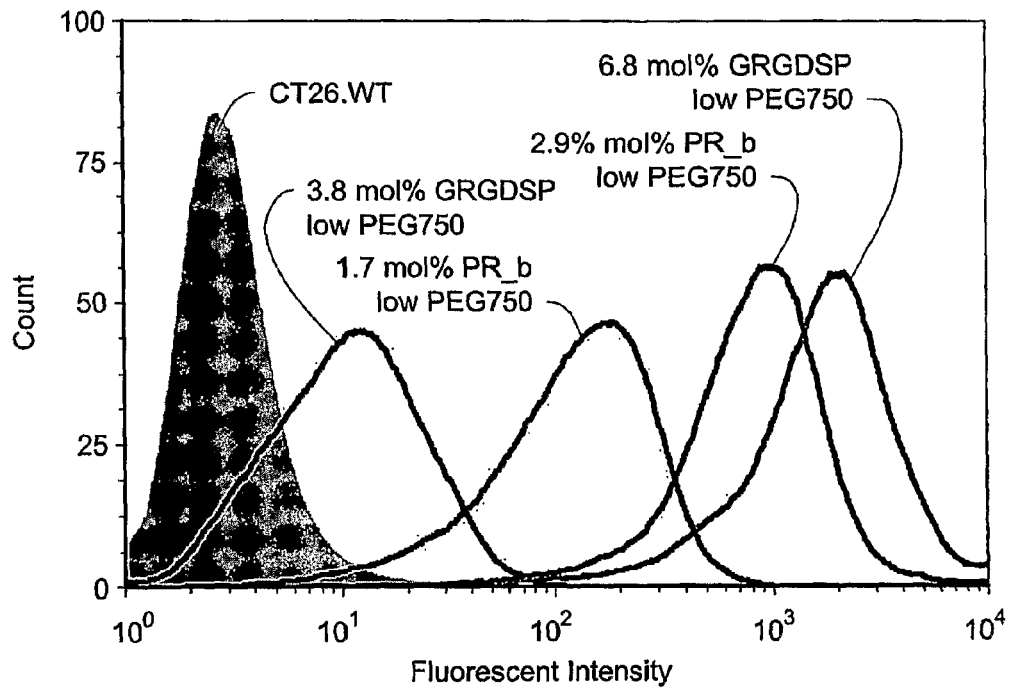

PR_b versus GRGDSP targeting. PR_b functionalized liposomes were compared to GRGDSP functionalized liposomes in FIG. 12. FIG. 12a shows that PR_b-functionalized liposomes outperform GRGDSP-functionalized liposomes, since PR_b liposomes give better binding with significantly lower concentrations compared to GRGDSP formulations. For example, a 9.0 mmol % GRGDSP liposome formulation gives equivalent binding to a 2.7 mol % PR_b liposome formulation and a 0.9 mol % PR_b liposome formulation outperforms a 5.3 mol % GRGDSP liposome formulation in terms of binding affinity. When low concentration of PEG750 in incorporated in the design (FIG. 12b) results show that 3.8 mol % GRGDSP is less effective then 1.3 mol % PR_b, and 6.8 mol % GRGDSP shows similar or slightly better binding than 2.9 mol % PR_b. Addition of low concentration of PEG2000 to GRGDSP systems (FIG. 12c) significantly decreases cell binding compared to PR_b formulations. A 2.5 mol % GRGDSP and low PEG2000 system shows minimal binding, while a 2.4 mol % concentration of PR_b and low PEG2000 shows significantly better performance with approximately two orders of magnitude increase of binding. A 4.6 mol % GRGDSP low PEG2000 system does show some increase in binding over a 2.5 mol % GRGDSP system but still is outperformed by both 1.2 and 2.4 mol % PR_b low PEG2000. These results demonstrate the superiority of our novel PR_b targeting over the GRGDSP-based targeting. Both the PR_b peptide amphiphile and PEG molecules are incorporated in the liposome membrane and high binding efficiency can be achieved by optimization of amounts PEG and peptide in parallel.

Figure 12C:
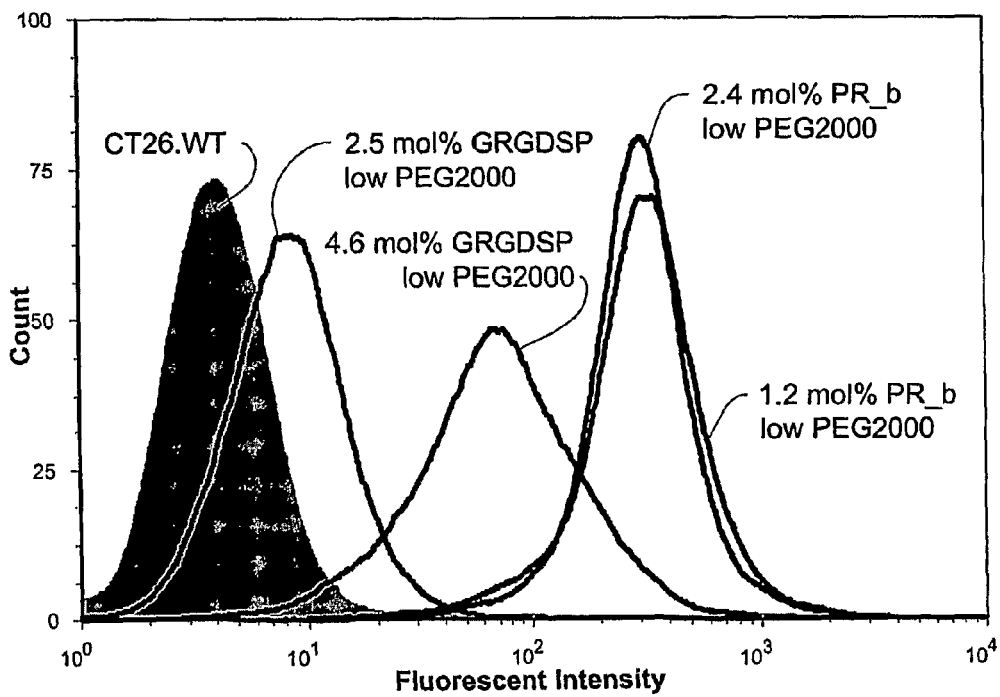
Figure 13:
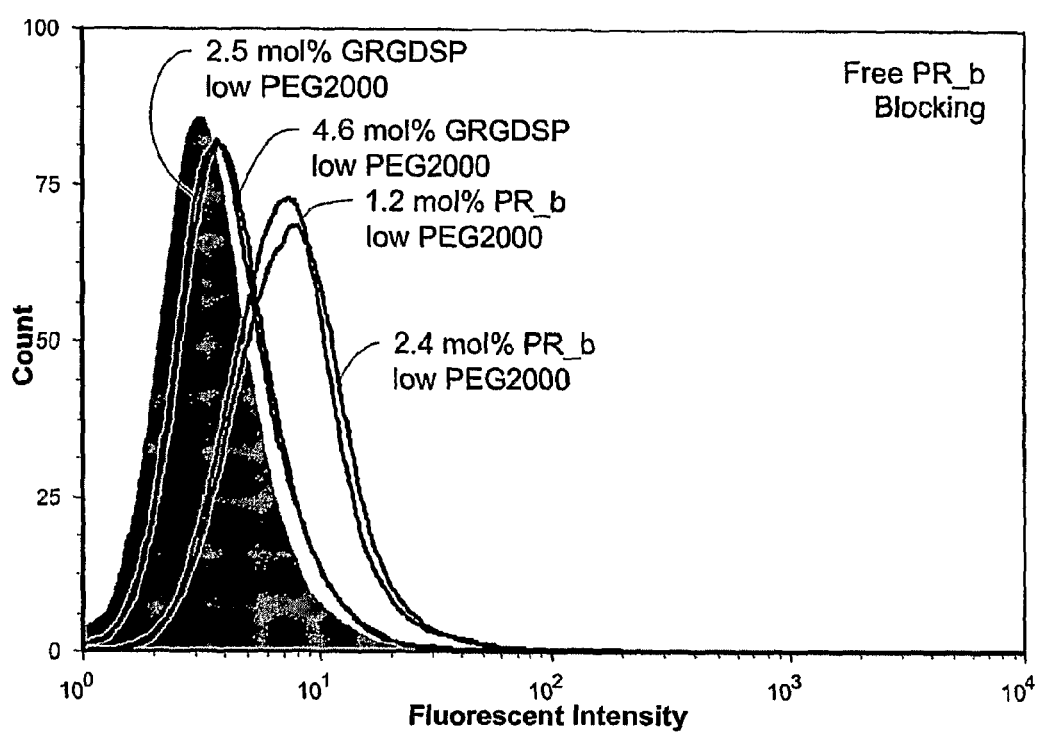
FIG. 13. Binding of PR_b and GRGDSP-targeted liposomes with low concentrations of PEG2000 to CT26.WT cells was blocked by incubating the cells with PR_b at a concentration of 200 μg/ml for 1 hr at 4° C. before incubating the cells with liposomes for 1 hr at 4° C. Cell adhesion was completely blocked in the presence of the free peptide.

Blocking binding of PR_b and GRGDSP targeted stealth liposomes using free PR_b peptide. PR_b peptide is a specific ligand for the integrin $\alpha_5\beta_1$ (see Example 1). In order to establish that binding of PR_b targeted stealth liposomes to colon cancer cells is specific for integrin $\alpha_5\beta_1$ colon cancer cells were incubated with an excess of free peptide-amphiphile for 1 hr prior to incubating them with the liposomes for another 1 hr at 4° C. Flow cytometry studies without any blocking with free peptide were also performed for the same formulations for 1 hr at 4° C. and results were similar to the ones shown in FIG. 12c. FIG. 13 shows flow cytometry results from blocking experiments for PR_b and GRGDSP targeted stealth liposomes with low concentrations of PEG2000 using free PR_b peptide amphiphile at a concentration of 200 µg/ml. Comparison of FIGS. 12c and 13 shows that addition of the excess free peptide completely blocks the binding of the functionalized stealth liposomes to CT26.WT cells. Therefore, we can conclude that the cell binding is $\alpha_5\beta_1$ mediated.

Endocytosis of PR_b and GRGDSP targeted stealth liposomes by CT26.WT cells. Binding of targeted liposomes is only one aspect for the development of an effective drug delivery system. These liposomes also need to be taken up (endocytosed) by the target cells. In order to characterize endocytosis of PR_b and GRGDSP-targeted stealth liposomes by CT26.WT cells, a confocal laser scanning microscope was used. Our data demonstrate that at all the times and temperatures examined binding and internalization of stealth liposomes (with no peptide attached), with low concentration of PEG750 and PEG2000 is minimal. GRGDSP stealth liposomes (3.3 mol % GRGDSP low PEG750 and 4.6 mol % GRGDSP low PEG2000) show very limited surface binding at 4° C.; however, some evidence of internalization can be seen at 37° C. internalization was seen only at 37° C., since endocytosis mechanisms do not operate at 4° C., and was greater at 24 hours compared to 3 hours. One possible explanation for this is that 24 hours of incubation allows more time for the recycling of integrins and thereby increasing the amount of endocytosed liposomes. Similar trends are observed for PR_b-targeted stealth liposomes (1.7 mol % PR_b low PEG750 and 2.4 mol % PR_b low PEG2000); except there is significantly higher level of internalization at 37° C. and surface binding at 4° C. Internalization studies at 37° C. show that even at 3 hours of incubation the amount of liposomes found in the cell cytoplasm was high and at 24 hours, this effect was even more pronounced. Almost the entire cytoplasmic region was stained with the endocytosed vesicles. Our data further demonstrate that when the PR_b peptide was used for targeting, a greater number of stealth liposomes were internalized with only half the concentration of GRGDSP. These confocal images illustrate $\alpha_5\beta_1$ mediated internalization of PR_b-targeted stealth liposomes by the colon cancer cells. These results also support the binding studies from the flow cytometry experiments and show that PR_b targeting can significantly improve the performance of stealth liposomes as compared to conventional GRGDSP targeting techniques.

Conclusions

In this study we have engineered a targeted delivery system that deliver a therapeutic load to colon cancer cells using a peptide sequence (PR_b) that can specifically target the integrin used with high affinity. The PR_b targeted stealth liposome system is capable of binding specifically to the integrin ask expressed on colon carcinoma cells and undergo cellular internalization via $\alpha_5\beta_1$ integrin-mediated pathways. We have optimized the delivery of the nanovector by first varying the amounts of both the peptide and PEG molecules on the liposome surface and studying the effect of concentration on binding to the colon cancer cells. Our results are well correlated and the trends are logical based on our understanding of the effect of PEG and peptide-amphiphile on the liposome interface. Increasing the amount of PR_b peptide enhances the binding affinity of liposomes and increasing the amount of PEG reduces it. When PEG2000 is incorporated in the peptide functionalized liposomes, the binding efficiency of the liposomes decreases compared to PEG750. We have shown that by optimizing the concentrations of peptide-amphiphile and PEG on the liposome interface, significant levels of binding can be achieved even when target functionality is implanted in parallel with PEG. PR_b targeting is superior to GRGDSP targeting as shown by improved binding and internalization at lower concentrations of PR_b. For example, liposomes with 9.0 mol % GRGDSP are required to perform comparably to 2.7 mol % PR_b liposomes. When PEG is incorporated in the design of the GRGDSP-functionalized liposome system, the performances degrades considerably, while the PR_b-targeted liposomes show only a small decrease in binding. Furthermore, PR_b-targeted stealth liposomes can internalize in significantly higher amounts than the GRGDSP-targeted stealth liposomes. Based on the above findings, we conclude that PR_b-targeted stealth liposomes can be potentially used in-vivo, to deliver a therapeutic load (DNA or other chemotherapy agents) directly to cancer cells and may help overcome side effects possible in nontargeted treatments.

Example 4

The Example presents the experiments conducted to determine the PEG concentrations in stealth liposomes. PEG concentrations were determined using methods available in the art.

Complexation with Barium Chloride and Iodine (Childs, *Microchemical Journal*, 1975; 20:190-192; Gebicki, *Acta Biochimica Polonica*, 2000; 47:901-911; Sims, *Analytical Biochemistry*, 1980; 107:60-63; Skoog, *Vox Sanguinis*, 1979; 37:345-349; and Selisko, *Journal of Chromatography*, 1993; 641:71-79): This method is a colorimetric assay based on a complex formation barium-iodide with PEG which produces a band at 535 nm. However, this assay suffers due to formation of precipitate in the samples during estimation. Sample wells could not be directly measured over a plate reader because the precipitate formation hindered the light path during the absorbance measurement. Measuring the absorbance of supernatant after centrifuging the samples did not yield any conclusive results. Formation of precipitates could be due to the presence of lipids and peptides. Therefore an additional step for precipitating out the lipids and proteins using trichloroacetic acid was included. However on measuring absorbance the readings for all samples were well within the standard deviation of each other and therefore amount of PEG could not be estimated.

Ferrothiocyanate Method (Nag, *Analytical Biochemistry*, 1996; 237:224-231; Nag, *Analytical Biochemistry*, 1997; 250:35-43). This method is also a colorimetric assay based on the partitioning of a chromophore present in the ammonium ferrothiocyanate from an aqueous to an organic phase in the presence of PEG. For estimation of PEG in stealth liposomes enzymatic digestion of lipids was employed using phopholipase C to prevent interference from phospholipids. The organic phase was separated from the aqueous phase by centrifuging the mixture and then the absorbance of the organic phase was measured. The results from the absorbance measurements did not have any correlation with the sample. Experimental error was very high in this experiment as the chromophore can easily diffuse from the organic to the aqueous phase even on slight tapping of the sample. Since Nag et al. have successfully used this method for estimation of PEG at higher concentrations, this method may not suitable for low concentrations of PEG.

Picric Acid Method (Shimada, *International Journal of Pharmaceutics*, 2000; 203:255-263): This method is another colorimetric assay based on the partitioning of a chromophore present in the sodium nitrate picrate solution, from an aqueous to an organic phase in the presence of PEG. This method requires significant amounts of sample which makes it difficult to work with based on the concentrations prepare for the experiments described herein. Also standard deviations were very high due to the possibility of mixing when separating the aqueous and the organic layers.

Bradford Assay (Allen, *Biochimica Et Biophysica Acta*, 1991; 1066:29-36): This assay detects PEG using the peptide bond present on lipidated PEG molecules (one per molecule).

This method also employs significant amounts of sample volume. Additionally, due to the presence of peptide in the liposomes the PEG signal gets masked. From the assay results we did not find any correlation in absorbance measurements, either in the samples or the calibration curves which leads to that this method is not suitable at our working concentrations.

Example 5

Figure 14A:
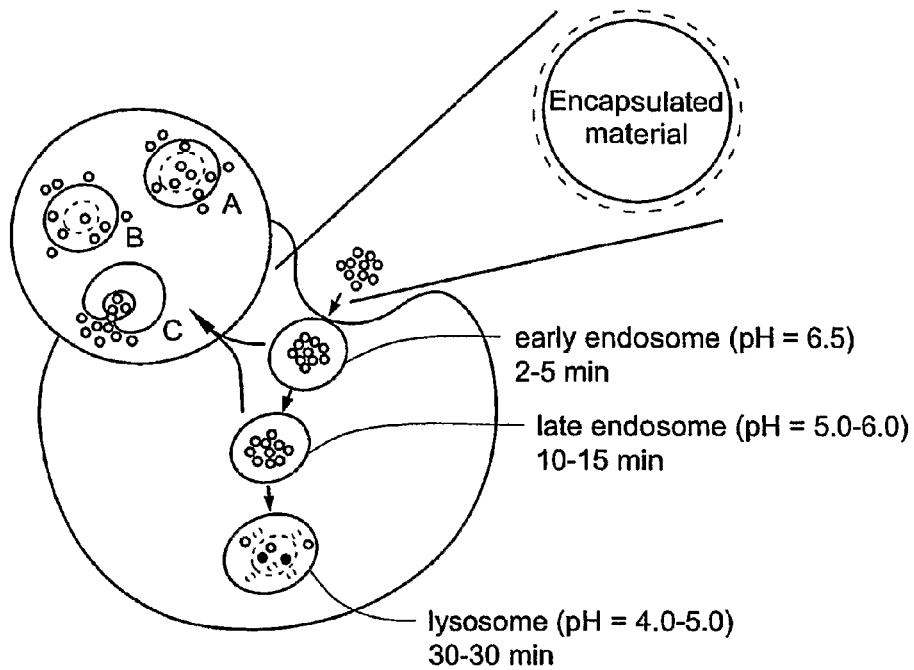
FIG. 14. A. Schematic of internalization and intracellular delivery of pH-sensitive liposomes (Simoes et al., *Advanced Drug Delivery Reviews*, 2004; 56(7):947-965). B. Calcein release from pH-sensitive (59% DOPE:35% CHEMS:4% PR_b:2% PEG2000 mole %) and non pH-sensitive liposomes (59% DPPC:35% cholesterol:4% PR_b:2% PEG2000 mole %) as a function of pH and incubation time.

This example presents the synthesis of pH-sensitive liposomes and evaluation of release of cargo by the liposomes as a function of pH.

pH-sensitive liposomes were produced that included dioleoylphosphatidylethanol-amines (DOPE), and mildly acidic amphiphiles such as cholesteryl hemisuccinate (CHEMS) in the following ratios: 59% DOPE:35% CHEMS:4% PR_b:2% PEG2000 mole %. Non pH-sensitive formulations had 59% DPPC:35% cholesterol:4% PR_b:2% PEG2000 mole %. The pH-sensitive and non pH sensitive liposomes were made using, methods described in Example 3. Calcein was encapsulated in liposomes at a self-quenching concentration of 80 mM. Liposome samples at a lipid concentration of 250 µM were added to a 96 well plate at pH~7.4. A control of lysed liposome were also added to a 96 well plate at a lipid concentration of 250 µM and at pH7.4. The control liposome was lysed by adding 0.1% Triton X-100. The plate was allowed to equilibrate at a constant temperature of 37° C. for 10 minutes before measuring fluorescence at pH~7.4 (t=0 min). In order to mimic the intracellular delivery pathway (FIG. 14a, see also Simoes et al., *Adv. Drug Deliv. Rev.*, 2004; 56(7): 947-965) liposomes and lysed liposomes (to account for the effect of pH on calcein fluorescence) were exposed to different pHs in sequence. A small amount a 1 N HCl was added to change the pH to 6.5. The pH of the plate was then changed to 5.5, and 4.5. Fluorescence intensities were measured immediately after the pH was adjusted and at times of interest.

Figure 14B:
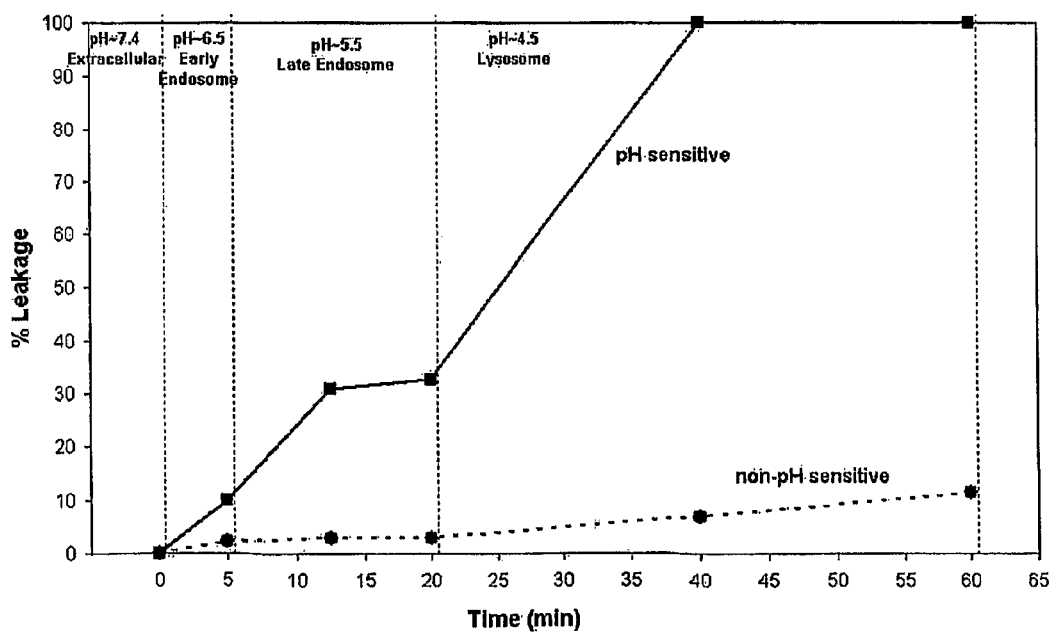

FIG. 14b shows that incubation of non pH-sensitive formulations functionalized with 4% PR_b and 2% PEG2000 at pH 6.5-4.5, that mimicked the intracellular delivery pathway, resulted in insignificant leakage of calcein (11% leakage) from the liposomes, whereas incubation of pH-sensitive formulations functionalized with 4% PR_b and 2% PEG2000, at the same pH and for the same incubation time, resulted in 100% release of calcein.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Sequence Listing Free Text

X1X2X3RX4 (SEQ ID NO:1) X1 is any amino acid, X2 is any amino acid, X3 is any amino acid, and X4 is any amino acid.

What is claimed is:

1. A biologically active compound comprising a headgroup, wherein the headgroup comprises PHSRNSGSGSGSGSGRGDSP (SEQ ID NO:8), and wherein the biologically active compound binds an $\alpha_5\beta_1$ integrin.

2. The biologically active compound of claim 1 wherein the biologically active compound further comprises a spacer attached to the amino terminus of the headgroup.

3. The biologically active compound of claim 2 wherein the spacer comprises KSS.

4. The biologically active compound of claim 1 wherein the headgroup further comprises KSS attached to the amino terminal end of the PHSRNSGSGSGSGSGRGDSP (SEQ ID NO:8).

5. The biologically active compound of claim 1 wherein the compound further comprises a tail, wherein the tail is attached to the headgroup.

6. The biologically active compound of claim 5 wherein the tail is hydrophilic.

7. The biologically active compound of claim 5 wherein the tail is hydrophobic.

8. The biologically active compound of claim 5 wherein the tail is amphipathic.

9. The biologically active compound of claim 5 wherein the tail further comprises a spacer present between the tail and the headgroup.

10. The biologically active compound of claim 1 wherein the biologically active compound specifically binds an $\alpha_5\beta_1$ integrin.

11. A composition comprising the biologically active compound of claim 1.

12. The composition of claim 11 wherein the composition further comprises a pharmaceutically acceptable carrier.

13. The biologically active compound of claim 2 wherein the spacer comprises amino acids.

14. A surface comprising the biologically active compound of claim 1, wherein the biologically active compound is covalently attached to the surface.

15. The surface of claim 14 wherein the biologically active compound is present on the surface at a concentration of at least 0.5 mol %.

16. The surface of claim 14 wherein the surface is 2-dimensional.

17. The surface of claim 14 wherein the surface is 3-dimensional.

18. A vesicle comprising the biologically active compound of claim 1, wherein the biologically active compound is present on the surface of the vesicle.

19. The vesicle of claim 18 wherein the biologically active compound is present on the surface at a concentration of at least 0.5 mol %.

20. The vesicle of claim 18 further comprising polyethylene glycol on the surface of the vesicle.

21. The vesicle of claim 20 wherein the polyethylene glycol is present at a concentration of at least 0.5 mol %.

22. The vesicle of claim 18 further comprising a trigger that promotes destabilization of the vesicle.

23. The vesicle of claim 22 wherein the trigger is a pH sensitive trigger or a temperature sensitive trigger.

24. The vesicle of claim 22 wherein the vesicle comprises dioleoylphosphatidylethanolamine.

25. The vesicle of claim 18 wherein the vesicle comprises a compartment comprising an aqueous liquid.

26. The vesicle of claim 25 wherein the aqueous liquid comprises an agent.

27. The vesicle of claim 26 wherein the agent is therapeutic.

28. The vesicle of claim 26 wherein the agent is nontherapeutic.

29. A composition comprising the vesicle of claim 18 and a pharmaceutically acceptable carrier.

30. A nanofiber comprising the biologically active compound of claim 1, wherein the biologically active compound is present on the surface of the nanofiber.

31. The nanofiber of claim 30 wherein the biologically active compound is present on the surface at a concentration of at least 0.5 mol %.

32. A method comprising contacting a membrane with the vesicle of claim 18, wherein the membrane comprises an $\alpha_5\beta_1$ integrin.

33. The method of claim 32 wherein the membrane is part of a cell.

34. The method of claim 33 wherein the cell is ex vivo.

35. The method of claim 33 wherein the cell is in vivo.

* * * * *

```
SEQUENCE LISTING

<160> NUMBER OF SEQ ID NOS: 12

<210> SEQ ID NO 1
<211> LENGTH: 5
<212> TYPE: PRT
<213> ORGANISM: artificial
<220> FEATURE:
<223> OTHER INFORMATION: based on synergy site PHSRN present in human
      fibronectin
<220> FEATURE:
<221> NAME/KEY: MISC_FEATURE
<222> LOCATION: (1)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid

<400> SEQUENCE: 1

Xaa Xaa Xaa Arg Xaa
1               5
```

```
<210> SEQ ID NO 2
<211> LENGTH: 8
<212> TYPE: PRT
<213> ORGANISM: artificial
<220> FEATURE:
<223> OTHER INFORMATION: linker of a headgroup situated between the
      synergy site and the RGD

<400> SEQUENCE: 2

Ser Gly Ser Gly Ser Gly Ser Gly
1               5

<210> SEQ ID NO 3
<211> LENGTH: 10
<212> TYPE: PRT
<213> ORGANISM: artificial
<220> FEATURE:
<223> OTHER INFORMATION: linker of a headgroup situated between the
      synergy site and the RGD

<400> SEQUENCE: 3

Ser Gly Ser Gly Ser Gly Ser Gly Ser Gly
1               5                   10

<210> SEQ ID NO 4
<211> LENGTH: 10
<212> TYPE: PRT
<213> ORGANISM: artificial
<220> FEATURE:
<223> OTHER INFORMATION: linker of a headgroup situated between the
      synergy site and the RGD

<400> SEQUENCE: 4

Gly Gly Gly Gly Gly Gly Gly Gly Gly Gly
1               5                   10

<210> SEQ ID NO 5
<211> LENGTH: 10
<212> TYPE: PRT
<213> ORGANISM: artificial
<220> FEATURE:
<223> OTHER INFORMATION: linker of a headgroup situated between the
      synergy site and the RGD

<400> SEQUENCE: 5

Ser Ser Ser Ser Ser Ser Ser Ser Ser Ser
1               5                   10

<210> SEQ ID NO 6
<211> LENGTH: 6
<212> TYPE: PRT
<213> ORGANISM: artificial
<220> FEATURE:
<223> OTHER INFORMATION: a negative control peptide

<400> SEQUENCE: 6

Gly Arg Gly Glu Ser Pro
1               5

<210> SEQ ID NO 7
<211> LENGTH: 6
<212> TYPE: PRT
<213> ORGANISM: artificial
<220> FEATURE:
<223> OTHER INFORMATION: an RGD region that mimics the cell adhesion
      domain of fibronectin

<400> SEQUENCE: 7
```

```
Gly Arg Gly Asp Ser Pro
1               5

<210> SEQ ID NO 8
<211> LENGTH: 20
<212> TYPE: PRT
<213> ORGANISM: artificial
<220> FEATURE:
<223> OTHER INFORMATION: a peptide having the components synergy site-
      linker-RGD

<400> SEQUENCE: 8

Pro His Ser Arg Asn Ser Gly Ser Gly Ser Gly Ser Gly Ser Gly Arg
1               5                   10                  15

Gly Asp Ser Pro
            20

<210> SEQ ID NO 9
<211> LENGTH: 23
<212> TYPE: PRT
<213> ORGANISM: artificial
<220> FEATURE:
<223> OTHER INFORMATION: a peptide having the components synergy site-
      linker-RGD

<400> SEQUENCE: 9

Lys Ser Ser Pro His Ser Arg Asn Ser Gly Ser Gly Ser Gly Ser Gly
1               5                   10                  15

Ser Gly Arg Gly Asp Ser Pro
            20

<210> SEQ ID NO 10
<211> LENGTH: 5
<212> TYPE: PRT
<213> ORGANISM: artificial
<220> FEATURE:
<223> OTHER INFORMATION: synergy site present in human fibronectin

<400> SEQUENCE: 10

Pro His Ser Arg Asn
1               5

<210> SEQ ID NO 11
<211> LENGTH: 21
<212> TYPE: PRT
<213> ORGANISM: artificial
<220> FEATURE:
<223> OTHER INFORMATION: a peptide having the components RGD-linker-
      synergy site

<400> SEQUENCE: 11

Arg Gly Asp Gly Gly Gly Gly Gly Gly Gly Gly Gly Gly Gly Gly Gly
1               5                   10                  15

Pro His Ser Arg Asn
            20

<210> SEQ ID NO 12
<211> LENGTH: 21
<212> TYPE: PRT
<213> ORGANISM: artificial
<220> FEATURE:
<223> OTHER INFORMATION: a negative control peptide having scrambled
      components

<400> SEQUENCE: 12

Arg Asp Gly Gly Gly Gly Gly Gly Gly Gly Gly Gly Gly Gly Gly Gly
```

-continued

```
1               5               10              15
His Pro Arg Asn Ser
            20
```